United States Patent [19]

Ruggeri et al.

[11] Patent Number: 5,340,727
[45] Date of Patent: Aug. 23, 1994

[54] GPIBα FRAGMENTS AND RECOMBINANT DNA EXPRESSION VECTORS

[75] Inventors: Zaverio M. Ruggeri, La Jolla; Jerry L. Ware, Encinitas, both of Calif.

[73] Assignee: The Scripps Research Institute, La Jolla, Calif.

[21] Appl. No.: 613,083

[22] Filed: Nov. 14, 1990

Related U.S. Application Data

[63] Continuation-in-part of Ser. No. 460,674, Jan. 4, 1990, abandoned, which is a continuation-in-part of Ser. No. 121,454, Nov. 17, 1987, abandoned.

[51] Int. Cl.$^5$ .................. C12N 15/12; C12N 15/85; A61K 37/02
[52] U.S. Cl. .................. 435/69.6; 435/69.8; 435/70.3; 435/172.3; 435/240.2; 435/320.1; 536/23.5; 530/381; 514/8; 514/822; 935/11; 935/27; 935/36; 935/56; 935/70; 935/71
[58] Field of Search .............. 435/69.8, 69.6, 70.3, 435/172.3, 240.2, 320.1; 530/381; 935/11, 27, 36, 56, 70, 71; 514/8, 822; 536/23.5

[56] References Cited

U.S. PATENT DOCUMENTS

| | | | |
|---|---|---|---|
| 4,664,884 | 5/1987 | Hawiger et al. | 514/13 |
| 4,766,075 | 8/1988 | Goeddel et al. | 435/240.2 |
| 4,880,788 | 11/1989 | Moake et al. | 514/150 |

OTHER PUBLICATIONS

Lopez, J. A. et al. "Cloning of the α-chain of human platelet ..." Proc. Natl. Acad. Sci. 84: 5615–5619 (Aug. 1987).
Handa, M. et al., "The von Willebrand Factor-binding Domain ..." J. Biol. Chem. 261(27):12579–12585 (Sep. 1986).
Michelson, A. D., et al., "Partial Characterization of a Binding ..." Blood 67(1): 19–26 (Jan. 1986).
Glover, D. M., "Gene Cloning: The Mechanics of DNA Manipulation" pp. 179–218 (1984).

*Primary Examiner*—Robert A. Wax
*Assistant Examiner*—Rebecca Prouty
*Attorney, Agent, or Firm*—Synnestvedt & Lechner

[57] ABSTRACT

Recombinant DNA expression vectors encoding a peptide which inhibits binding of von Willebrand factor to platelet membrane glycoprotein Ib, said vector including a nucleotide sequence encoding the amino acid sequence from $HIS^1$ to $LEU^{610}$, inclusive, of the amino terminal region of platelet membrane glycoprotein Ibα, or any sequential subset thereof; mammalian host cells transformed by said vectors; and a process for producing a peptide having the identifying characteristics of the 45 kDa tryptic fragment of glycocalicin comprising the steps of (A) providing a stable, extrachromosomally replicable vector capable of directing in mammalian cells the expression of a nucleotide sequence encoding an amino acid sequence which includes said fragment, said nucleotide sequence further encoding as part of said amino acid sequence amino acids which are not native to said fragment, and which are oriented at the carboxy terminus of said fragment, (B) transforming said mammalian cells with said vector, and (C) maintaining said transformed mammalian cells under conditions permitting the expression of said peptide.

19 Claims, 7 Drawing Sheets

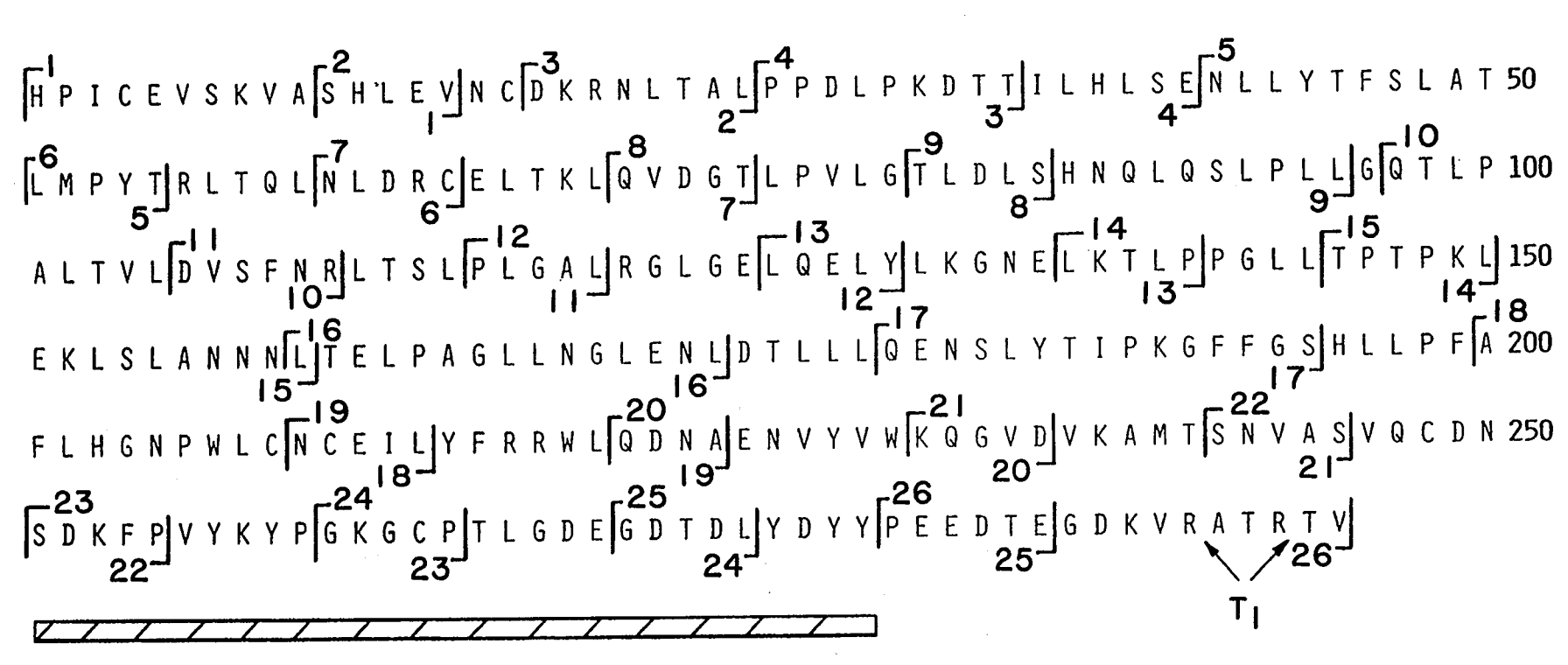

FIG. IA

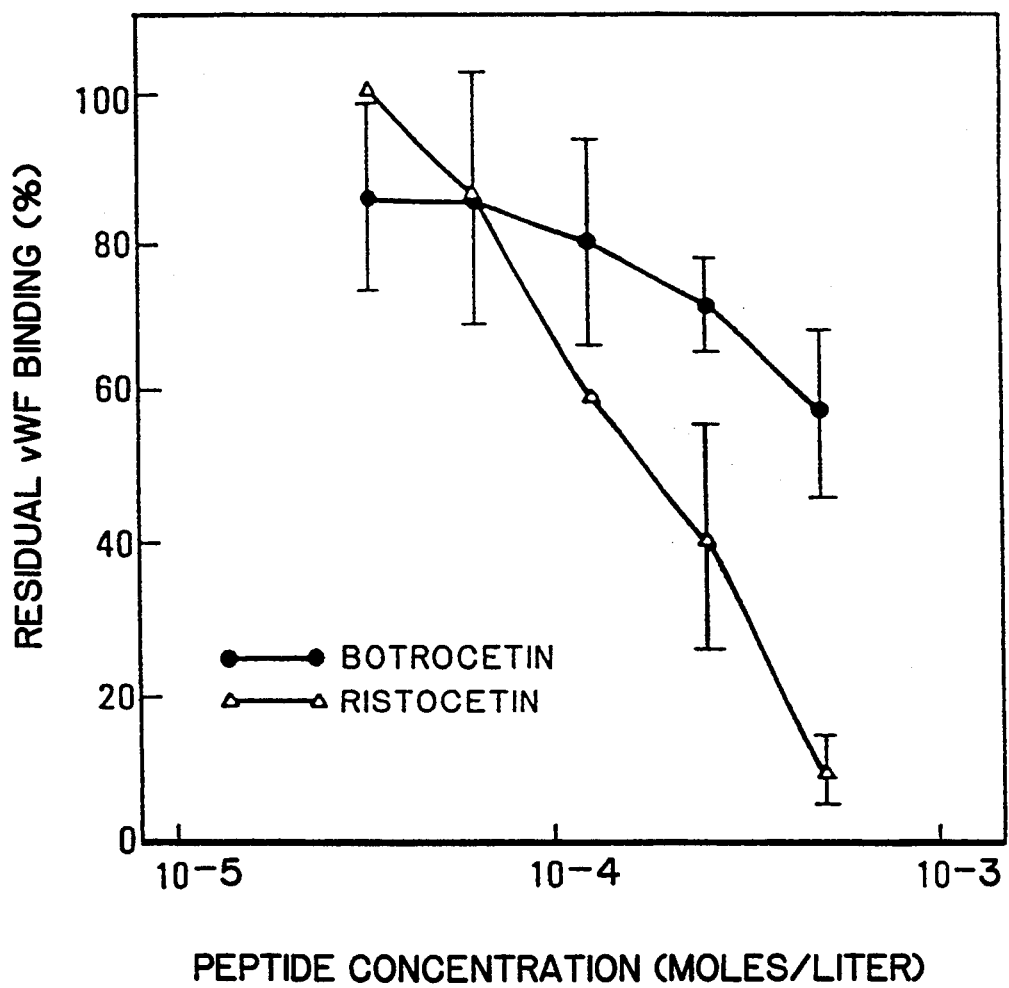

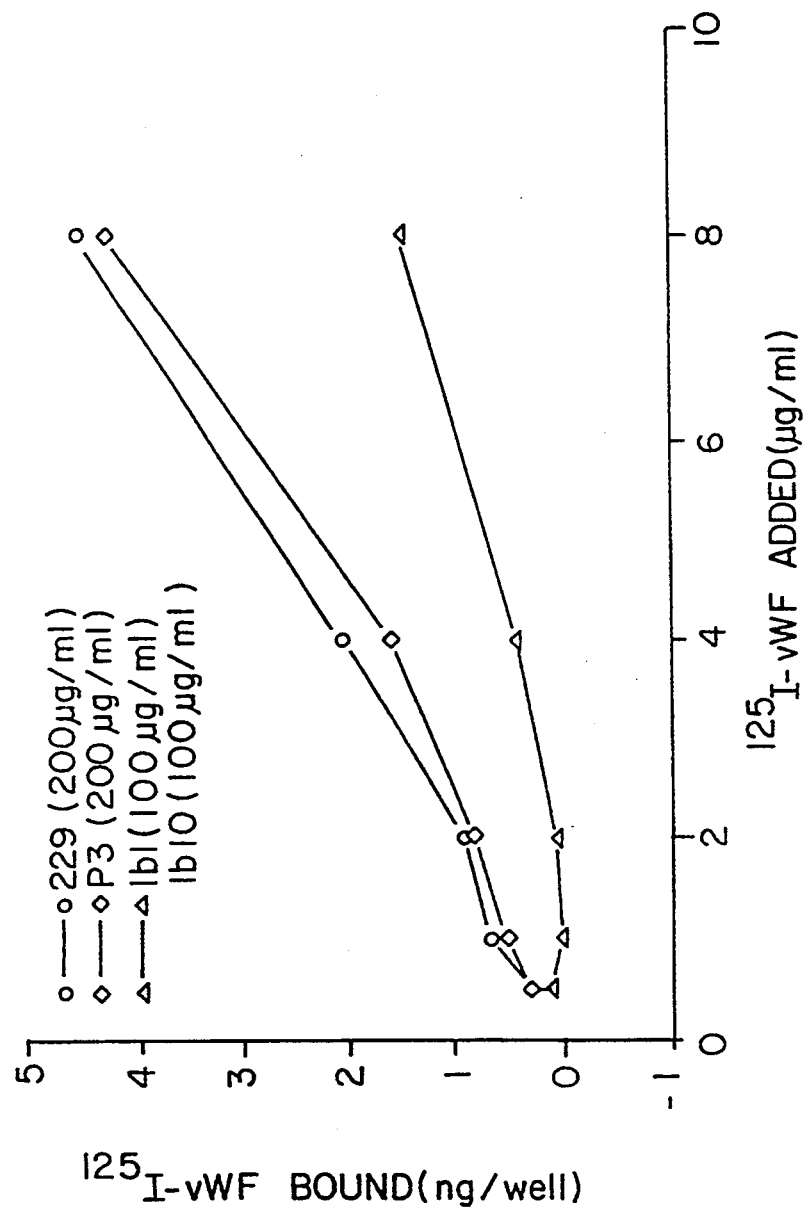

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
     ( A ) LENGTH: 320
     ( B ) TYPE: Amino Acid
     ( C ) STRANDEDNESS: Not applicable
     ( D ) TOPOLOGY: Linear ( x i ) SEQUENCE DESCRIPTION: SEQ ID NO: 1:

```
His  Pro  Ile  Cys  Glu  Val  Ser  Lys  Val  Ala
               5                              10

Ser  His  Leu  Glu  Val  Asn  Cys  Asp  Lys  Arg
               15                             20

Asn  Leu  Thr  Ala  Leu  Pro  Asp  Leu  Pro
               25                             30

Lys  Asp  Thr  Thr  Ile  Leu  His  Leu  Ser  Glu
               35                             40

Asn  Leu  Leu  Tyr  Thr  Phe  Ser  Leu  Ala  Thr
               45                             50

Leu  Met  Pro  Tyr  Thr  Arg  Leu  Thr  Gln  Leu
               55                             60

Asn  Leu  Asp  Arg  Cys  Glu  Leu  Thr  Lys  Leu
               65                             70

Gln  Val  Asp  Gly  Thr  Leu  Pro  Val  Leu  Gly
               75                             80

Thr  Leu  Asp  Leu  Ser  His  Asn  Gln  Leu  Gln
               85                             90

Ser  Leu  Pro  Leu  Leu  Gly  Gln  Thr  Leu  Pro
               95                             100

Ala  Leu  Thr  Val  Leu  Asp  Val  Ser  Phe  Asn
               105                            110

Arg  Leu  Thr  Ser  Leu  Pro  Leu  Gly  Ala  Leu
               115                            120

Arg  Gly  Leu  Gly  Glu  Leu  Gln  Glu  Leu  Tyr
               125                            130

Leu  Lys  Gly  Asn  Glu  Leu  Lys  Thr  Leu  Pro
               135                            140

Pro  Gly  Leu  Leu  Thr  Pro  Thr  Pro  Lys  Leu
               145                            150
```

```
                    Glu Lys Leu Ser Leu Ala Asn Asn Asn Leu
                            155                 160

Thr Glu Leu Pro Ala Gly Leu Leu Asn Gly
                            165                 170

Leu Glu Asn Leu Asp Thr Leu Leu Leu Gln
                            175                 180

Glu Asn Ser Leu Tyr Thr Ile Pro Lys Gly
                            185                 190

Phe Phe Gly Ser His Leu Leu Pro Phe Ala
                            195                 200

Phe Leu His Gly Asn Pro Trp Leu Cys Asn
                            205                 210

Cys Glu Ile Leu Tyr Phe Arg Arg Trp Leu
                            215                 220

Gln Asp Asn Ala Glu Asn Val Tyr Val Trp
                            225                 230

Lys Gln Gly Val Asp Val Lys Ala Met Thr
                            235                 240

Ser Asn Val Ala Ser Val Gln Cys Asp Asn
                            245                 250

Ser Asp Lys Phe Pro Val Tyr Lys Tyr Pro
                            255                 260

Gly Lys Gly Cys Pro Thr Leu Gly Asp Glu
                            265                 270

Gly Asp Thr Asp Leu Tyr Asp Tyr Tyr Pro
                            275                 280

Glu Glu Asp Thr Glu Gly Asp Lys Val Arg
                            285                 290

Ala Thr Arg Thr Val Val Lys Phe Pro Thr
                            295                 300

Lys Ala His Thr Thr Pro Trp Gly Leu Phe
                            305                 310

Tyr Ser Trp Ser Thr Ala Ser Leu Asp Ser
                            315                 320
```

( 2 ) INFORMATION FOR SEQ ID NO: 2:

( i ) SEQUENCE CHARACTERISTICS:
        ( A ) LENGTH: 31
        ( B ) TYPE: Nucleic acid
        ( C ) STRANDEDNESS: single stranded
        ( D ) TOPOLOGY: Linear ( x i ) SEQUENCE DESCRIPTION: SEQ ID NO: 2:

```
            G AAT CTG ACA GCG CTG CCT CCA GAC CTG CCG         31
              Asn                             Pro
              21                              30
```

( 2 ) INFORMATION FOR SEQ ID NO: 3:

( i ) SEQUENCE CHARACTERISTICS:
        ( A ) LENGTH: 20
        ( B ) TYPE: Nucleic acid
        ( C ) STRANDEDNESS: single stranded
        ( D ) TOPOLOGY: Linear ( x i ) SEQUENCE DESCRIPTION: SEQ ID NO: 3:

```
               CAG GGC ACC AAG AGG CAG CG                     20
          Leu               Leu
          120               115
```

( 2 ) INFORMATION FOR SEQ ID NO: 4:

( i ) SEQUENCE CHARACTERISTICS:
        ( A ) LENGTH: 24
        ( B ) TYPE: Nucleic acid
        ( C ) STRANDEDNESS: single stranded
        ( D ) TOPOLOGY: Linear ( x i ) SEQUENCE DESCRIPTION: SEQ ID NO: 4:

```
        GGATCCACTC  AAGGCTCCCT  TGCC                    24
```

( 2 ) INFORMATION FOR SEQ ID NO: 5:

( i ) SEQUENCE CHARACTERISTICS:
        ( A ) LENGTH: 20
        ( B ) TYPE: Nucleic acid
        ( C ) STRANDEDNESS: single stranded
        ( D ) TOPOLOGY: Linear ( x i ) SEQUENCE DESCRIPTION: SEQ ID NO: 5:

```
        GC  TTT  GGT  GGG  GAA  CTT  GAC              20
        Lys                       Val
        301                       296
```

GPIBα FRAGMENTS AND RECOMBINANT DNA EXPRESSION VECTORS

This invention was made with government support under government contract HL-42846 awarded by the National Institutes of Health. The government has certain rights in the invention.

CROSS-REFERENCE TO RELATED APPLICATIONS

This is a continuation-in-part of copending application Ser. No. 07/460,674, filed on Jan. 4, 1990, now abandoned, which is a continuation-in-part of copending application Ser. No. 07/121,454, filed on Nov. 17, 1987, now abandoned.

The invention described and claimed in the aforementioned '674 application relates to a class of peptides useful for inhibiting the binding of von Willebrand factor (vWF) to platelet membrane glycoprotein Ib (GPIb). The present application is concerned with the subject matter of the '674 application and also with novel DNA expression vectors encoding peptides useful for inhibiting the binding of vWF to GPIb, such peptides including peptides of the type referred to in the '674 application.

FIELD OF THE INVENTION

This invention relates to (A) peptides which inhibit the binding of von Willebrand factor to platelet membrane glycoprotein Ib and GPIb expressed on the surface of any cell of megakaryocytic lineage; (B) the use of these peptides in the prevention of platelet activation, aggregation and surface adhesion; and (C) to the use of these peptides in the prevention of thrombosis. The present invention relates also to (D) recombinant DNA expression vectors which encode peptides which inhibit binding of vWF to GPIb, wherein the peptides include the amino terminal region of platelet membrane glycoprotein Ibα (GPIbα), or any sequential subset thereof; and (E) host cells transformed by such vectors. These vectors are useful in the production of peptides which can be used, for example, in the prevention of platelet activation, aggregation and surface adhesion, and also in the prevention of thrombosis.

When conditions such as, for example, trauma, surgery or disease disrupt the vascular endothelial lining, thereby exposing the subendothelial connective tissue to blood, the initial hemostatic response is platelet plug formation, also known as "primary hemostasis." One of the critical events in this process is the adhesion of platelets to the exposed subendothelial tissue. vWF mediates this adhesion by binding both to the GPIb receptor found on the surface of the platelet membrane and also to the subendothelial collagen fibrils found in the vascular subendothelium. This action by vWF enables platelet adhesion to occur under the conditions of high shear stress often found in damaged or diseased tissue, as caused by, for example, high flow rate in small vessels. This is of critical importance in stopping blood loss from capillaries, small arterioles and venules.

The importance of the interaction between vWF and GPIb is suggested by the bleeding diathesis of Bernard-Soulier syndrome, a disorder characterized by decreased quantities or abnormal function of GPIb and, consequently, markedly reduced platelet adhesion due to the inability of vWF to bind with GPIb.

Inhibition of vWF-GPIb interaction would thus be expected to result in the prevention of primary hemostasis and the induction of an anti-thrombotic state useful in prevention of diseases in which occlusion of blood vessels plays an important role. The proteolytic fragments of GPIb and peptides produced using the vectors of the present invention have the ability to act as anti-thrombotic agents by their prevention of the binding of vWF to GPIb.

By way of background, it is noted that GPIb is a two-chain molecule having an apparent molecular mass of approximately 160 kDa. GPIb is composed of a heavy (alpha, or GPIbα) chain, having a molecular mass of approximately 145 kDa linked by disulfide bonds to a light (beta, or GPIbβ) chain, having a molecular mass of approximately 22 kDa. GPIb is an integral membrane protein and both the alpha- and beta- chains described above have transmembrane domains. Proteolysis by an endogenous calcium-dependent platelet protease generates a proteolytic fragment from the amino-terminal portion of GPIbα, which is known as glycocalicin and which consists of nearly the entire GPIbα chain, having an approximate molecular mass of 140 kDa. This fragment originates from the extracellular domain of GPIbα and is water soluble. Thus, it is released after cleavage from the parent molecule.

A complete cDNA encoding human GPIbα polypeptide has been determined by Lopez et al., *Proc. Natl. Acad. Sci. USA*, 84, 5615–5617 (1987), a publication which is not prior art. For convenience, the amino acid numbering system of Lopez et al., above, is followed herein. Also, the gene for GPIbα has been cloned from a genomic cosmid library utilizing a partial cDNA clone as a probe, and its sequence, including introns, has been determined by Wenger, *Biochemical and Biophysical Research Communications*, 156(1), 389–395 (1988). The nucleotide numbering system of Wenger, above, is followed herein.

The predicted GPIbα sequence consists of a 16 amino acid signal peptide, MET$^{-16}$ through PRO$^{-1}$, followed by a 610 amino acid mature peptide region, HIS$^1$ through LEU$^{610}$. As shown in Table I below (see also FIG. 1 and SEQ ID NO: 1), the complete sequence of the 45 kDa tryptic fragment comprises HIS$^1$ through ARG$^{290}$ or ARG$^{293}$. For the purposes of this application, as GPIbα and glycocalicin have the same amino terminus and are nearly identical in size, references to glycoalicin fragments and GPIbα fragments herein should be considered equivalent.

Trypsin has been previously shown to cleave glycocalicin between residues ARG$^{290}$/ALA$^{291}$ and/or ARG$^{293}$/THR$^{294}$ to generate two fragments, one of which has an apparent molecular mass of 45 kDa and extends from the amino terminal residue HIS$^1$ to ARG$^{290}$ or ARG$^{293}$; the other, with an apparent molecular mass of 84 kDa, is very rich in carbohydrate and represents the carboxyl terminal half of glycocalicin beginning at ALA$^{291}$ or THR$^{294}$. The 45 kDa fragment consists of a single-chain species and a two-chain species. The latter is generated by an additional tryptic cleavage between residues LYS$^{237}$ and ALA$^{238}$ yielding two polypeptides of apparent molecular mass 35 kDa and 7 kDa, held together by one or more interchain disulfide bonds. The relative proportions of the one- and two-chain species depend on the extent of tryptic cleavage of glycocalicin. For example, after digestion for 18 hours with an enzyme to substrate ratio of 1:200 (w/w), the two-chain species predominates. The two chains of this species can be separated by reduction of the disulfide bonds and end-blocking of the resulting sulfhydryl groups, for example, by treatment with a molar excess of dithiothreitol and by S-carboxyimidomethylation with iodoacetamide, respectively.

SUMMARY OF THE INVENTION

As set forth in aforementioned application Ser. No. 07/470,674, there are provided peptides comprising any peptide of the 45 kDa amino terminal tryptic fragment of glycocalicin selected from the amino acid sequence shown below in Table I:

TABLE I

```
         10           20           30           40           50           60
          |            |            |            |            |            |
HPI CEVS KVAS HLEVNCDKRNL TALPP DLPKDTTI LHLS ENLLYTFS LATLMP YTRLTQL 70           80           90          100          110          120
          |            |            |            |            |            |
NLDRCEL TKLQVDGTLP VLGTLDLS HNQLQS LPLLGQTLP ALTVLDVS FNRLTS LPLGAL 130          140          150          160          170          180
          |            |            |            |            |            |
RGLGELQEL YLKGNELKTLP PGLLTPTP KLEKLS LANNNLTELP AGLLNGLENLDTLLLQ 190          200          210          220          230          240
          |            |            |            |            |            |
ENSLYTI PKGFFGS HLLPFAFLHGNP WLCNCEI LYFRRWLQDNAENVYVWKQGVDVKAMT 250          260          270          280          290
          |            |            |            |            |
S NVAS VQCDNS DKFPVYKYP GKGCP TLGDEGDT DLYDYYP EEDTEGDKVRATR
``` and which inhibit the binding of von Willebrand factor to platelet membrane glycoprotein Ib and/or GPIb expressed on the surface of any cell of megakaryocytic lineage.

The invention further comprises any sequential subset of the 45 kDa amino terminal tryptic fragment of glycocalicin selected from the foregoing amino acid sequence which inhibits binding of vWF to GPIb and/or GPIb expressed on the surface of any cell of megakaryocytic lineage.

In addition, the invention comprises a peptide which inhibits binding of vWF to GPIb and/or GPIb expressed on the surface of any cell of megakaryocytic lineage selected from the group of peptides consisting of:

DKRNLTALPPDLPKDTT;
NLTALPPDLPKDTTI; PPDLPKDTTILHLSE;
PGLLTPTPKLEKLSL; KQGVDVKAMTSNVAS;
GDTDLYDYYPEEDTE;
EEDTEGDKVRATRTV; PPDLPKDTT; and EEDTE.

An additionally preferred peptide is a peptide of any sequential subset of amino acids of a peptide which inhibits binding of vWF to GPIb and/or GPIb expressed on the surface of any cell of megakaryocytic lineage.

The invention further comprises peptides having the general formula $(KR)_n$, wherein n=2-10 or $R_n$, wherein n=2-20 and any derivatives thereof which inhibit binding of vWF to GPIb and/or GPIb expressed on the surface of any cell of megakaryocytic lineage.

The invention comprises also a method for inhibiting activation of platelets, adhesion of platelets to surfaces, or aggregation of platelets to each other with an effective amount of one of the aforementioned peptides or subsets, or other polymers as described therein.

Another aspect of the invention comprises a method for inhibiting thrombosis in a patient which comprises administering to said patient an effective amount of one of the aforementioned peptides or subsets, or other polymers as described therein.

As also set forth in the aforementioned '674 parent application, a complete cDNA encoding human GPIbα polypeptide has been determined by Lopez et al. With such information, a nucleotide sequence can be inserted into an appropriate vector for the expression of peptides from the 45 kDa fragment. Accordingly, another aspect of the invention is the provision of a recombinant DNA expression vector encoding a peptide which inhibits binding of vWF to GPIb, said vector including a nucleotide sequence encoding the amino acid sequence from $HIS^1$ to $LEU^{610}$, inclusive of the amino terminal region of GPIbα, or any sequential subset thereof. In preferred form, the vector includes a nucleotide sequence which encodes a peptide including the aforementioned $HIS^1$ amino acid of GPIbα. Particularly preferred are those vectors including a nucleotide sequence which endcodes a peptide including the amino acid sequence from $HIS^1$ to $THR^{294}$, inclusive, of GPIbα.

Still another aspect of the invention relates to a recombinant DNA expression vector encoding a peptide which includes, and extends beyond, at the carboxyl terminal region, the 45 kDa tryptic fragment of glycocalicin, and which, upon expression in a suitable transformed host cell, produces a peptide having the identifying characteristics of the aforementioned 45 kDa fragment.

The invention relates also to a host cell which has been transformed by any the aforementioned vectors. Particularly preferred host cells include mammalian host cells.

Another aspect of the invention relates to a process for producing peptides having the identifying characteristics of the 45 kDa tryptic fragment of glycocalicin comprising maintaining any of the aforementioned transformed host cells under conditions permitting the expression of the peptide.

BRIEF DESCRIPTION OF THE DRAWINGS

FIGS. 1A and 1B show the inhibitory effect of peptide subfragments of the 45 kDa amino terminal region of GPIbα on ristocetin-dependent and botrocetin-dependent vWF binding to platelet GPIb receptors. FIG. 1a shows the peptide subfragments used in this experiment. FIG. 1b shows the inhibitory effect of the various peptide subfragments on ristocetin-dependent and botrocetin-dependent vWF binding to platelet GPIb receptors.

FIG. 3 is a graph which shows the inhibitory effects of the GPIbα peptide fragment consisting of residue positions 251 through 279 on botrocetin-dependent and ristocetin-dependent vWF binding to platelet GPIb receptors.

FIG. 6 is a graph which shows that the GPIbα antigen produced by pMW2 is functionally active in a botrocetin-induced binding assay.

DETAILED DESCRIPTION OF THE INVENTION

Figure 1B:
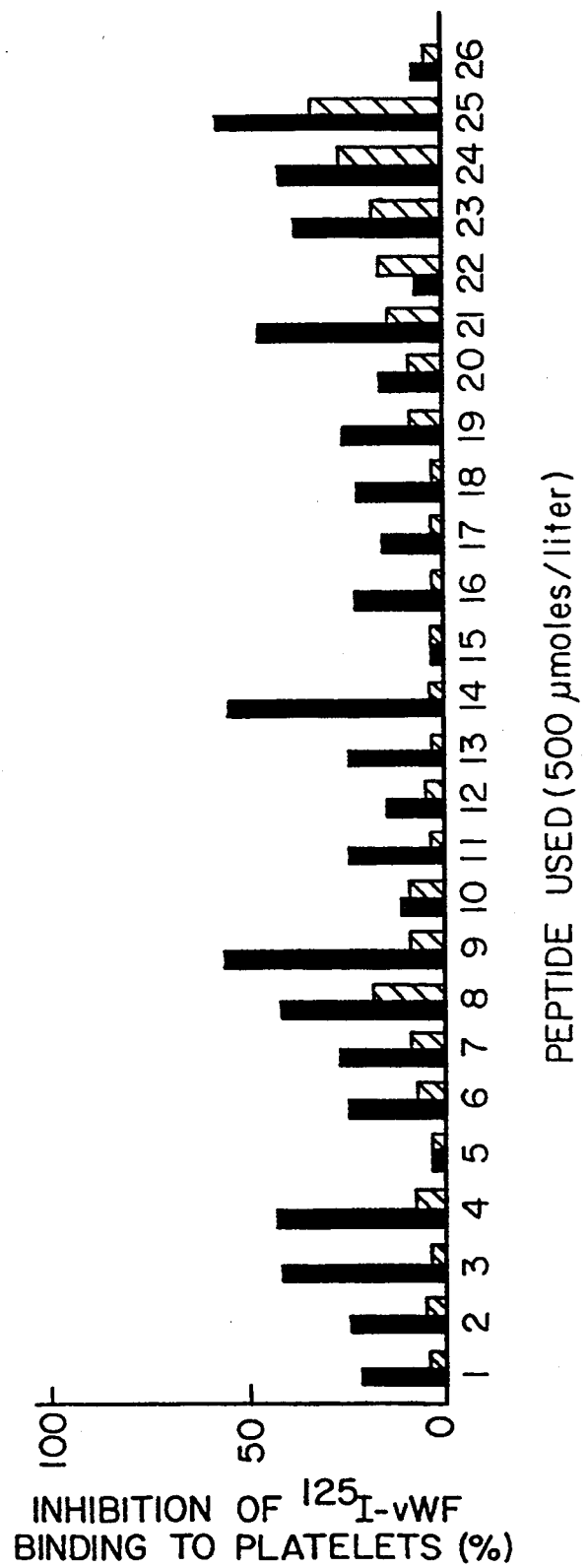

For purposes of this disclosure, accepted short-hand designations of the amino acids have been used. The designations are shown in Table II below.

TABLE II

| One and three-letter Amino Acid abbreviations | | |
| --- | --- | --- |
| A | ALA | Alanine |
| C | CYS | Cysteine |
| D | ASP | Aspartic Acid |
| E | GLU | Glutamic Acid |
| F | PHE | Phenylalanine |
| G | GLY | Glycine |
| H | HIS | Histidine |
| I | ILE | Isoleucine |
| K | LYS | Lysine |
| L | LEU | Leucine |
| M | MET | Methionine |
| N | ASN | Asparagine |
| P | PRO | Proline |
| Q | GLN | Glutamine |
| R | ARG | Arginine |
| S | SER | Serine |
| T | THR | Threonine |
| V | VAL | Valine |
| W | TRP | Tryptophan |
| Y | TYR | Tyrosine |
| B | ASX | Asp or Asn, not distinguished |
| Z | GLX | Glu or Gln, not distinguished |
| X | X | Undetermined or atypical amino acid |

DEFINITIONS

Unless indicated otherwise herein, the following terms have the indicated meanings.

Codon—A DNA sequence of three nucleotides (a triplet) which encodes through mRNA an amino acid, a translation start signal or a translation termination signal. For example, the DNA nucleotide triplets TTA, TTG, CTT, CTC, CTA and CTG encode the amino acid leucine (LEU); TAG, TAA and TGA are translation stop signals; and ATG is a translation start signal encoding methionine (MET).

Structural Gene—A DNA sequence which encodes through its corresponding messenger RNA (mRNA) a sequence of amino acids characteristic of a specific polypeptide. Structural genes may also have RNA as their primary product, for example, transfer RNA (tRNA) or ribosomal RNA (rRNA).

Transcription—The process of producing RNA from a structural gene.

Translation—The process of producing a polypeptide from mRNA.

Coding Sequence (Encoding DNA)—DNA sequences which, in the appropriate reading frame, code for the amino acids of a protein. For the purpose of the present invention, it should be understood that the synthesis or use of a coding sequence may necessarily involve synthesis or use of the corresponding complementary strand, as shown by: 5'-CGG.GGA.GGA-3' which has a complementary strand which is 3'-GCC.CCT.CCT-5' and which encodes the tripeptide NH$_2$-arg-gly-gly-CO$_2$H. A discussion of or claim to one strand is deemed to refer to or to claim the other strand and the double stranded counterpart thereof as is appropriate, useful or necessary in the practice of the art.

cDNA—A DNA molecule or sequence which has been enzymatically synthesized from the sequence(s) present in an mRNA template.

Transcribed Strand—The DNA strand whose nucleotide sequence is read 3'→5' by RNA polymerase to produce mRNA. This strand is also referred to as the noncoding strand.

Non-Transcribed Strand—This strand is the antiparallel compliment of the transcribed strand and has a base sequence identical to that of the mRNA produced from the transcribed strand except that thymine bases are present (instead of uracil bases of the mRNA). It is referred to as "coding" because, like mRNA, and when examined 5'→3' the codons for translation may be directly discerned. This strand is also referred to as the coding strand.

Expression—The process undergone by a structural gene to produce a product. In the case of a protein product, it is a combination of transcription and translation.

Recombinant DNA Molecule—A molecule consisting of segments of DNA from different genomes which have been joined end-to-end and have, or can be modified to have, the capacity to infect some host cell and be maintained therein.

Biological Activity—One or more functions, effects of, activities performed or caused by a molecule in a biological context (that is, in an organism or in an in vitro facsimile). A characteristic biological activity of the amino terminal region of GPIbα is the ability to bind to vWF, an activity which may be demonstrated in vitro, for example, by the aggregation of platelets in the presence of ristocetin.

Reducing Conditions—Refers to the presence of a "reducing" agent in a solution containing vWF, or polypeptides derived therefrom, which agent causes the disruption of disulfide bonds of the vWF. However, consistent with usage typical in the art, the reducing agent, such as, for example, dithiothreitol (DTT), causes a vWF disulfide bond to be broken by forming a disulfide bond between a vWF cysteine and the DTT with no net change in oxidation state of the involved sulfur atoms.

Phage or Bacteriophage—A bacterial virus, many of which consist of DNA sequences encapsulated in a protein envelope or coat (capsid).

Promoter—A DNA sequence upstream from a gene which promotes its transcription.

Plasmid—A nonchromosomal double-stranded DNA sequence comprising an intact replicon such that the plasmid is replicated in a host cell. When the plasmid is placed within a procaryotic or eucaryotic host cell, the characteristics of that cell may be changed (or transformed) as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant."

Cloning—The process of obtaining a population of organisms, or DNA sequences or other macromolecules derived from one such organism or sequence by asexual reproduction or DNA replication.

Expression Plasmid—A plasmid into which has been inserted the DNA being cloned, such as the vWF structural gene. The DNA sequence inserted therein may also contain sequences which control the translation of mRNA resultant therefrom, and may contain restriction endonuclease sites which facilitate assembly of, and may facilitate further modification of, the expression plasmid. An expression plasmid is capable of directing, in a host cell, the expression therein of the encoded polypeptide and usually contains a transcription promoter upstream from the DNA sequence of the encoded structural gene. An expression plasmid may or may not become integrated into the host chromosomal DNA. For the purpose of this invention, an integrated plasmid is nonetheless referred to as an expression plasmid.

Viral Expression Vector—A viral expression vector is similar to an expression plasmid except that the DNA may be packaged into a viral particle that can transfect cells through a natural biological process.

Downstream—A nucleotide of the transcribed strand of a structural gene is said to be downstream from another region of the gene if the nucleotide is normally read by RNA polymerase after the other region of the gene. The complimentary nucleotide of the nontranscribed strand, or the corresponding base pair within the double stranded form of the DNA, are also denominated downstream.

Additionally, and making reference to the direction of transcription and of translation within the structural gene, a restriction endonuclease sequence added upstream (or 5') to the gene means it is added before the sequence encoding the amino terminal end of the protein, while a modification created downstream (or 3') to the structural gene means that it is beyond the carboxy terminus-encoding region thereof.

Glycoprotein Ibα or GPIbα—It is understood that all references herein to Glycoprotein Ibα refer to human GPIbα.

Mature GPIbα—Refers to a polypeptide consisting of the amino acid sequence HIS$^1$ to LEU$^{610}$ which is typically found in platelets as a transmembrane protein. Additionally, when expressed in mammalian cells, mature GPIbα is usually glycosylated.

Signal Peptide (Sequence)—A signal peptide is the sequence of amino acids in a newly translated polypeptide which signals translocation of the polypeptide across the membrane of the endoplasmic reticulum and into the secretory pathway of the cell. A signal peptide typically occurs at the beginning (amino terminus) of the protein and is 20–40 amino acids long with a stretch of approximately 5–15 hydrophobic amino acids in its center. Typically the signal sequence is proteolytically cleaved from the protein during, or soon after, the process of translocation into the endoplasmic reticulum. That portion of a gene or cDNA encoding a signal peptide may also be referred to as a signal sequence.

In the course of work on the present invention, purified glycocalicin was used in tests to evaluate the effectiveness of compounds in inhibiting the binding of von Willebrand factor to intact platelets.

Purified glycocalicin has been produced by a two-step procedure based on 1) affinity chromatography using wheat germ agglutinin insolubilized onto Sepharose ® beads; and 2) subsequent immunoaffinity chromatography using a monoclonal antibody (LJ-P3) directed against glycocalicin and insolubilized onto Sepharose ® beads.

Outdated platelet concentrates were used as starting material for the purification of glycocalicin. Plasma components were eliminated by sedimenting the platelets at 2,300 g for 25 minutes at room temperature (22°–25° C.) removing the supernatant, and resuspending the platelet pellet in a buffer composed of 10 mM Tris base and 150 mM NaCl, adjusted to pH 7.4 with HCl (Tris-buffered saline; TBS), and containing 2 mM EDTA. This procedure was repeated twice. After the first wash, the suspension was centrifuged at 600 g for 1 minute and the pellet containing most of the contaminating red cells was discarded before continuing with the washing procedure. After the last centrifugation, the platelets were resuspended in TBS containing 2 mM CaCl$_2$ and 0.1 mM phenylmethylsulfonyl fluoride (PMSF). They were then disrupted by sonication (three pulses of 15 seconds each at approximately 100 watts, with the platelet suspension kept on ice). The suspension was then left for three hours at room temperature and for 16–18 hours at 4° C., always with continuous stirring. Following this, the particulate material in the suspension was removed by centrifugation at 100,000 g for 20 minutes at 12° C. The clear supernatant was applied to a column (2.6 cm in diameter and 11 cm high) of wheat germ agglutinin bound to Sepharose ® beads activated with cyanogen bromide and equilibrated with TBS containing 1 mM EDTA, 0.1 mM PMSF, and 0.02% sodium azide. The column was washed with a volume of buffer corresponding to twice the volume of beads before eluting bound proteins with 100 mM N-acetyl glucosamine added to the same buffer. The whole procedure was performed at room temperature. The eluted material was immediately applied to a monoclonal antibody column (5 cm in diameter and 2.5 cm high) consisting of purified IgG bound to Sepharose ® beads activated with cyanogen bromide. The monoclonal antibody used, designated LJ-P3, is specific for the glycocalicin portion of GPIb; its preparation, characterization, and purification are described in Handa et al., *J. Biol. Chem.*, 261, 12579–12585 (1986). The column was equilibrated with a buffer composed of 100 mM Tris base, 500 mM LiCl$_2$, 1 mM EDTA, 0.1 mM PMSF, 0.02% sodium azide, adjusted to pH 7.4 with HCl. The column was washed with a volume of buffer corresponding to three times the volume of the beads. Bound glycocalicin was eluted with 70–80 ml of 50 mM diethylamine containing 1 mM EDTA and 0.1 mM PMSF. During this step, the flow rate through the column was regulated so that elution was complete in 20–25 minutes. The whole procedure was performed at room temperature. The eluted glycocalicin was collected in 6 g of glycine to neutralize the high pH of diethylamine. The purified material was dialyzed extensively against TBS, concentrated with Aquacide ®, and again dialyzed with TBS. Purified glycocalicin was stored in aliquots at −70° C.

Purified glycocalicin was digested with trypsin pretreated with N-tosyl-L-phenylalanine chloromethylketone. The enzyme substrate ratio was 1:200 and the reaction was allowed to proceed for 16-18 hours at 37° C. At the end of the incubation, trypsin activity was inhibited with a two-fold molar excess of (p-amidinophenyl)methanesulfonyl fluoride. The 45 kDa fragment of glycocalicin generated by trypsin digestion was purified by gel permeation high performance liquid chromatography using one GF 450 and two GF 250 dupont Zorbax ® columns (9.4 mm in diameter by 25 cm in length) mounted in series. The columns were equilibrated with 200 mM $(NH_4)_2HPO_4$, pH 7, and the flow rate was 1 mE/minute. The procedure was performed at room temperature. The 45 kDa fragment eluted as a sharp peak and was then collected, concentrated with Aquacide ®, dialyzed extensively with TBS, and stored in aliquots at $-70°$ C. until used.

We have used the purified glycocalicin to demonstrate that this proteolytic fragment of GPIbα can inhibit the binding of vWF to intact platelets. The assay system is based on the use of $^{125}I$-labeled vWF and fresh or formalin-fixed platelets; ristocetin was used to induce the binding of vWF to GPIb. After incubation for 30 minutes at 37° C., without stirring, separation of bound platelet from free vWF ligand was achieved by centrifugation through 20% sucrose in Tyrode buffer, followed by measurement of the bound radioactivity as described in Ruggeri et al., *J. Clin. Invest.*, 72, 1-12 (1983). Nonspecific binding was evaluated for selected points by measuring the binding in the presence of a 40-fold excess of unlabeled vWF. Binding isotherms were evaluated by Scatchard-type analysis to determine binding parameters (including the estimate of nonspecific binding) using the computer-assisted program "Ligand" as described in Munson, *Methods Enzymol.*, 92, 542-576 (1983).

Glycocalicin at final concentrations in excess of 1 mg/ml can block the binding of $^{125}I$-labeled vWF to intact GPIb completely; the concentration necessary to inhibit 50% of the binding (denoted as the $IC_{50}$ value) averaged 150 μg/ml for seven different glycocalicin preparations.

Subsequently, all the intra-chain disulfide bonds present in glycocalicin were reduced by treatment with a molar excess of dithiothreitol and the resulting sulfhydryl groups blocked by S-carboxyimidomethylation. The resulting reduced and alkylated glycocalicin was found to retain the property of blocking vWF binding to intact GPIb on platelets in the presence of ristocetin. Since the reduced and alkylated glycocalicin had lost its secondary structure dependent on intra-chain disulfide bonds, this experiment demonstrated that the function of interacting with vWF could be ascribed to specific regions within the primary structure of glycocalicin.

The 45 kDa tryptic fragment of glycocalicin was purified using high performance liquid chromatography (abbreviated HPLC) and gel permeation columns that separate proteins on the basis of their molecular mass. Because of the conditions used for tryptic digestion, the 45 kDa fragment consisted essentially of the two-chain species. This purified proteolytic fragment of glycocalicin was used to test its ability to block the binding of vWF to the GPIb of platelets. The 45 kDa fragment inhibited completely the ristocetin-mediated binding of vWF to platelets, i.e. to GPIb, with an $IC_{50}$ of approximately 3.5 μM.

In a similar experiment, glycocalicin was digested with trypsin, the disulfide bonds were reduced with dithiothreitol and the resulting sulfhydryl groups S-carboxyimidomethylated with iodoacetamide. The 35 kDa amino terminal fragment was then purified by gel permeation HPLC and tested for its inhibitory effect on the binding of vWF to the GPIb of platelets in a ristocetin-mediated assay. Its $IC_{50}$ was found to be similar to that of the parent unreduced 45 kDa fragment. In accordance with the results obtained with whole glycocalicin, these results confirm that the primary structure of the amino terminal region of glycocalicin contains vWF binding domain(s) whose function does not depend on maintenance of the native three dimensional conformation of the molecule.

Following these findings, overlapping peptides of 15 amino acid residues each and representing the sequence of the entire 45 kDa amino terminal fragment of glycocalicin were synthesized. The following peptides were found to inhibit the binding of vWF to the GPIb of platelets with $IC_{50}$ values of 0.5 mM or better (single-letter notation is used for the identification of amino acid residues): DKRNLTALPPDLPKDTT; NLTALPPDLPKDTTI; PPDLPKDTTILHLSE (these three peptides overlap each other and cover the sequence between residues $ASP^{18}$ and $GLU^{40}$, inclusive of glycocalicin); PGLLTPTPKLEKLSL (residues $PRO^{141}$ to $LEU^{155}$); KQGVDVKAMTSNVAS (residues $LYS^{231}$ to $SER^{245}$); GDTDLYDYYPEEDTE; EEDTEGDKVRATRTV (these two peptides cover the sequence between residues $GLY^{271}$ and $VAL^{295}$, inclusive). The results, therefore, clearly indicate the existence of multiple domains within the amino terminal region of glycocalicin that have functional relevance for vWF binding.

Shorter peptides with sequences corresponding to overlapping regions of the longer peptides exhibiting inhibitory activity were also synthesized. Two of these shorter peptides were found to have inhibitory activity. Their sequences were PPDLPKDTT (residues $PRO^{26}$ to $THR^{34}$ of glycocalicin) and EEDTE (residues $GLU^{281}$ to $GLU^{285}$). These two peptides, when tested individually, had $IC_{50}$ values greater than 0.5 mM. When they were combined together at a concentration of 0.5 mM, however, they completely inhibited vWF binding to GPIb. This experiment demonstrates that different noncontiguous domains within the primary sequence of glycocalicin may co-participate synergistically in providing the vWF binding site(s) and, consequently, the vWF binding activity. The sequence of the 45 kDa amino terminal tryptic fragment of glycocalicin, therefore, as well as subsets of it (as shown above) contains information useful for designing molecules capable of inhibiting the binding of vWF to the GPIb of platelets.

Peptides of the general formula $(KR)_n$, where $n=2-7$, and the peptide $R_{11}$ also inhibit the interaction of vWF with GPIb. Peptides of the general formula $R_nRGDV$ or $(KR)_nRGDV$ were previously demonstrated to block fibrinogen binding to GPIIb/IIIa (U.S. Pat. No. 4,683,291, "Platelet Binding Inhibitors"). The latter peptides are now shown to be as effective in blocking vWF-GPIb interaction as their $(KR)n$ analogs and therefore represent a class of bifunctional antiplatelet agents.

The mechanisms responsible for triggering the binding of vWF to GPIb in vivo have not yet been determined. Normally, vWF and GPIb coexist in circulation without any significant interaction occurring. Contact with exposed or damaged subendothelium triggers binding and, possibly, vWF assumes an altered conformation (which is capable of complex formation) when contacting a blood vessel wall. See Sakariassen et al., *Nature*, 979, 636–638 (1979); Stel et al., *Blood*, 65, 85–90 (1985); and Turitto et al., *Blood*, 65, 823–831 (1985). Conformational changes necessary for binding may also be induced in GPIb by contact of the platelet with other blood components or exposure of the platelet to high sheer stress in a damaged vessel. Moake et al., *Blood*, 71, 1366–1374 (1988).

The interaction between vWF and GPIb can be demonstrated in vitro by several methods. Binding can be demonstrated in the presence of ristocetin, a glycopeptide antibiotic which may act by reducing excess negative charge density between the macromolecules. See Howard et al., *Thromb. Diath. Haemorrh.*, 26, 362–369 (1971); and Coller et al., *J. Clin. Invest.*, 60, 302–312 (1977).

The interaction may also be triggered by the presence of the protein botrocetin, a component of certain snake venoms. Read et al., *Proc. Nat'l. Acad. Sci. USA*, 75, 4514–4518 (1978).

The interaction between vWF and GPIb can also be enhanced by removing terminal (negatively charged) sialic acid carbohydrate residues from the vWF molecule. De Marco et al., *J. Clin. Invest.*, 68, 321–328 (1981).

The in vivo relevance of the known standard in vitro binding assays, and binding inhibition assays, is not yet known. A detailed investigation of the mechanisms of in vitro binding may eventually identify the in vivo mechanisms or important features thereof. The binding of vWF to GPIb as measured under the different experimental systems may also involve different functional domains of the macromolecules or conformational states thereof.

Consequently, it is reasoned that those peptides derived from GPIb that would be particularly useful as therapeutic inhibitors of vWF binding, in vivo, would be those peptides which demonstrate significant inhibition of vWF binding in more than one in vitro assay system.

In addition, it is reasoned that the domains of GPIbα, and in particular the domains of the 45 kDa amino terminal fragment thereof which are responsible for binding vWF, are not necessarily adjacent to one another along the linear sequence of the amino terminal polypeptide, but that binding to vWF is accomplished by peptide sequences scattered throughout the 45 kDa polypeptide which are brought into proximal positions when the amino terminal fragment assumes its native tertiary structure.

Additional developmental work which forms the basis of the present application was conducted in light of the above hypotheses. As is demonstrated below, polymers are revealed which have increased vWF binding inhibition activity.

The present invention includes within its scope a synthetic peptide assembled from multiple native sequence fragments of the amino terminal portion of glycocalicin, which fragments are not proximal in the primary structure and which have a structure whose tertiary conformation displays binding domains which mimic the three dimensional binding domains of GPIb and which have a high affinity for vWF.

In addition, the present invention encompasses therapeutic polymers with multiple domains of amino acid sequences from GPIb which domains are connected by a linker which may or may not be of peptide character.

In the practice of the present invention, it is preferred to use the following peptides, identified in Table III, below, as inhibitors of the interaction of vWF with platelets.

TABLE III

| peptide | residue positions in glycocalicin |
|---|---|
| (a) SDKFPVYKYPGKGCPTLGDEGDTDLYDYY | 251–279 |
| (b) NLDRCELTKLQVDGT | 61–75 |
| (c) QVDGTLPVLGTLDLS | 71–85 |
| (d) TLDLSHNQLQSLPLL | 81–95 |
| (e) QTLPALTVLDVSFNR | 97–111 |
| (f) LKTLPPGLLTPTPKL | 136–150 |
| (g) NCEILYFRRWLQDNA | 210–224 |
| (h) QDNAENVYVWKQGVD | 221–235 |
| (i) KQGVDVKAMTSNVAS | 231–245 |
| (j) SNVASVQCDNSDKFP | 241–255 |
| (k) SDKFPVYKYPGKGCP | 251–265 |
| (l) GKGCPTLGDEGDTDL | 261–275 |
| (m) GDTDLYDYYPEEDTE | 271–285 |

Of the aforementioned peptides, the use of (a) or (m) is particularly preferred and the use of (a) is most preferred.

These peptides, as well as other polymers within the scope of the present invention, can be used individually or in combination with one or more other polymers of the present invention (whether or not covalently attached) in the inhibition of platelet activation, aggregation, or adherence to surfaces, or as a potential therapeutic anti-thrombotic.

The present invention includes also within its scope a peptide comprising any sequential subset of the amino acid sequence of a peptide of (a) to (m) above and which inhibits binding of vWF to GPIb and/or GPIb expressed on the surface of any cell of megakaryocytic lineage.

Another aspect of the present invention encompasses a cysteine dimer of a peptide or other polymer within the scope of the present invention. Such dimers are compounds in which a cysteine residue of a peptide or polymer is covalently linked to a cysteine residue of another peptide or polymer by way of a disulfide bridge. A preferred cysteine dimer for use in the practice of the present invention is the dimer of the peptide SDKFPVYKYPGKGCPTLGDEGDTDLYDYY. It has been observed that under the in vitro conditions of vWF binding assays used in the present invention, the preferred dimer is particularly effective at inhibiting vWF binding.

Still another aspect of the present invention includes a polymer which inhibits binding of vWF to GPIb and/or GPIb expressed on the surface of any cell of megakaryocytic lineage and which includes the following domains:

domain A—a series of amino acids which constitutes any of the peptides of the present invention or of any subset of the amino acid sequence of said peptides;

domain B—a series of amino acids which constitutes any of the peptides of the present invention or of any subset of the amino acid sequence of said peptides and which may be the same or different from that of domain A; and domain C—a linker which joins domain A and domain B.

The linker which joins segments of the aforementioned polymer can comprise monomeric or polymeric units assembled from units such as, for example, methylene, vinyl, amino acids and dextrans. A preferred polymer for use in the practice of the present invention is one in which domain A comprises the peptide of (a) above and domain B comprises the peptide of (m) above. More preferably, there is used a polymer in which domain A comprises any subset of the amino acid sequence of the peptide of (a) above and domain B comprises any subset of the amino acid sequence of the peptide of (m) above.

It should be understood that polymers of the aforementioned types can include also one or more additional domains which impart desired functional properties to the polymer such as enhanced binding or solubility.

In addition, the present invention includes within its scope a synthetic polymer which inhibits binding of vWF to GPIb and/or GPIb expressed on the surface of any cell of megakaryocytic lineage and which comprises one or more sequences of amino acids of the GPIbα chain, said sequence(s) being normally positioned at or near the surface of the GPIbα chain in its native conformation and capable of interacting with vWF.

It should be understood that the present invention also includes within its scope derivatives of any of the peptides or other polymers of the present invention. Such derivatives include peptides or other polymers which have been modified by the addition of additional polymer sequence or by the addition of functional groups such as, for example, acetyl, glycosyl or ester moieties.

To carry out the assessments of this invention of the utility of numerous overlapping GPIbα peptides to inhibit binding of vWF to platelets, peptides based on the amino acid sequence of the 45 kDa amino terminal tryptic fragment of glycocalicin were synthesized as described by Houghton et al., *Proc. Natl. Acad. Sci. USA*, 82, 5135 (1985). See also Vicente et al., *J. Biol. Chem.*, 268(34), 18473–18479 (1988).

In the well known procedure for solid-phase synthesis of a peptide, the desired peptide is assembled starting from an insoluble support such as benzhydryl amine or chloromethylated resin (derived from cross-linked polystyrene, and available from chemical supply houses). The amino acid at the carboxy-terminal end of the desired peptide, carrying protecting groups on the α-amino nitrogen and on any other reactive sites, is attached to the resin from solution using known peptide coupling techniques. The protecting group on the alpha-amino group is removed (leaving other protecting groups, if any, intact), and the next amino acid of the desired sequence (carrying suitable protecting groups) is attached, and so on. When the desired peptide has been completely built up, it is cleaved from the resin support, all protecting groups are removed, and the peptide is recovered. Examples of suitable protecting groups include α-tert-butyloxycarbonyl for the α-amino-group; benzyl, 4-methoxybenzyl, or 4-methylbenzyl for the thiol group of cysteine, the β-carboxylic acid group of aspartic acid, the γ-carboxylic acid group of glutamic acid and the hydroxyl groups of serine, threonine, and tyrosine; benzyloxycarbonyl or a 2-chloro- or 3,4-dimethoxy- derivative thereof for the ring nitrogens of histidine and tryptophan and the e-amino group of lysine; p-nitrophenyl for the amide nitrogens of asparagine and glutamine; and nitro or tosyl for the guanadine group of arginine.

With regard to the cloning aspects of the invention, it is anticipated that GPIbα, or fragments thereof, could be cloned by any of the following strategies. If the cDNA sequence is available, then oligonucleotides can be chosen for PCR amplification of messenger RNA. This presumes the availability of a cell line expressing adequate levels of the mRNA. If the mRNA is thought to be rare, subtraction hybridization schemes can be employed to amplify the desired message before performing the specific PCR amplification. The oligos could also be used to amplify the sequence desired from genomic DNA assuming that the possible existance of intron sequences can either be easily determined or will not affect subsequent use of the clone.

If antibodies directed against the protein are available, then polysomes containing the mRNA can be precipitated, the mRNA purified and copied into ds cDNA which can then be cloned. If a cell line abundantly expresses the protein, then first a cDNA library could be constructed using an expression vector and then the library screened by antibody binding to expressing clones.

If the protein sequence is available, then oligonucleotides can be chosen that can be used to screen cDNA or genomic libraries. A mixed set of oligonucleotides will need to be chosen since the codon usage of amino acids will not precisely be known.

Elements necessary for the practice of the preferred embodiments of the invention are: (A) DNA sequences which encode the residue $HIS^1$-$LEU^{610}$ or $HIS^1$-$ALA^{302}$ domains of the GPIbα polypeptide; (B) an expression plasmid or viral expression vector capable of directing in a eucaryotic cell the expression therein of the aforementioned domains; and (C) a eucaryotic host cell in which said expression may be effected.

The GPIbα polypeptides so expressed are expected not to be secreted from host cells because of the lack of attachment to the nascent GPIbα polypeptide of a signal peptide. Purification of proteins expressed therein and the extraction of pharmacologically useful quantities thereof is expected to be more difficult than if the polypeptide could be caused to be secreted into the culture medium of the host cells.

It is expected that such expression systems are nonetheless useful for diagnostic assay purposes such as testing the proper function of vWF in a patient.

Accordingly, in the preferred practice of the invention there is provided a GPIbα encoding DNA sequence for insertion into a suitable host cell in which there is inserted upstream from the residue 1-610 or 1-302 encoding sequence thereof a DNA sequence encoding the GPIbα signal peptide. When attached to the amino terminal end of the residue 1-610 or 1-302 GPIb(α) polypeptide, the signal peptide causes the polypeptide to be recognized by cellular structures as a polypeptide of the kind to be processed for ultimate secretion from the cell, with concomitant cleavage of the signal polypeptide from the mature GPIbα polypeptide.

A wide variety of expression plasmids or viral expression vectors are suitable for the expression of the GPIbα polypeptides or the amino terminal regions thereof. One factor of importance in the selection of an expression system is the provision of a high efficiency transcription promoter directly adjacent to the cloned GPIbα insert.

Another factor of importance in the selection of an expression plasmid or viral expression vector is the provision of an antibiotic resistance gene marker therein so that continuous selection for stable transformant eucaryotic host cells can be applied.

Plasmids suitable in the practice of the invention include pCDM8, pCDM8$^{neo}$, pcDNA1, pcDNA1$^{neo}$, pMAM$^{neo}$ and Rc/CMV. Plasmids whose use in the practice of the invention is preferred include pCDM8$^{neo}$, pcDNA1$^{neo}$, pMAM$^{neo}$ and Rc/CMV.

There are several viral expression vector systems suitable for the practice of the invention including those based upon retroviruses and those based upon baculovirus *Autographa californica* nuclear polyhedrosis virus.

Representative host cells comprising permanent cell lines suitable for the practice of the invention include CHO-K1 Chinese hamster ovary cells, ATCC-CCL.61; COS-1 cells, SV-40 transformed African Green monkey kidney, ATCC-CRL 1650; ATT 20 murine pituitary cells; RIN-5F rat pancreatic β cells; cultured insect cells, *Spodoptera frugiperda*; or yeast (*Sarcomyces*).

Example 9 contains a detailed explanation of preferred procedures used to express and secrete the GPIbα polypeptide or the amino terminal domain thereof.

EXAMPLES

The following examples illustrate the biological activity of the peptides of the present invention and exemplary cloning methods useful in practicing the invention.

EXAMPLE 1

Inhibition of Ristocetin-Induced Binding of vWF to Platelets

To test the inhibitory activity of the peptides of the present invention, formalin-fixed platelets were used at a final concentration of $1 \times 10^{11}/l$. Assayed peptides were then added at various concentrations. One third final volume of vWF-deficient plasma was then added followed by $^{125}$I-vWF at a final concentration of 5 μg/ml. Ristocetin was then added at a concentration of 1.0 mg/ml. After incubation for o30 minutes at room temperature, bound and free vWF ligand were separated by centrifuging 50 μl of the mixture through 300 μl of 20% sucrose at 12,000 g for 4 minutes. The platelet pellet was then separated from the rest of the mixture to determine platelet-bound radioactivity. Nonspecific binding was defined as the residual binding of $^{125}$I-vWF in the presence of a 50-fold excess of unlabeled vWF but in the absence of any peptides.

Percent inhibition with a given peptide was calculated by dividing the specific cpm in the absence of peptide. The IC$_{50}$ values (concentration of peptide which inhibited binding by 50%) for the peptides tested are shown in Table IV, below.

TABLE IV

| (KR)$_7$ | 9 and 15 μM (two experiments) |
| (KR)$_5$ | 13 μM |
| (KR)$_3$ | 120 μM |
| (KR)$_2$ | 200 μM |
| (KR)$_4$GDV | 16 μM |
| (R)$_8$GDV | 6 μM |
| YRGDV | >600 μM (no inhibition seen) |

Complete inhibition was not seen with any of the peptides at the concentrations tested.

EXAMPLE 2

Inhibition of Asialo-vWF Binding to Fresh Platelets

Fresh platelets were prepared by drawing blood into a solution of 11 mM trisodium citrate and 2 mM EDTA. Platelet-rich plasma was then prepared by differential centrifugation. The platelet count was then adjusted to $1 \times 10^{11}/l$. Peptides were then added to various concentrations and $^{125}$I-asialo-vWF was then added at a final concentration of 5 μg/ml. After incubation for 30 minutes at room temperature, bound and free vWF ligand were separated by centrifuging 50 μl of the mixture through 300 μl of 20% sucrose at 12,000 g for 4 minutes. The platelet pellet was then separated from the rest of the mixture to determine platelet-bound radioactivity. Non-specific binding was defined as the residual binding of $^{125}$I- asialo-vWF in the presence of a 50-fold excess of unlabeled vWF but in the absence of any peptides.

Percent inhibition with a given peptide was calculated by dividing the specific cpm obtained when various concentrations of peptide were added by the specific cpm in the absence of peptide. The IC$_{50}$ values for the peptides tested are shown in Table V, below.

TABLE V

| (KR)$_7$ | 1.5 μM |
| (KR)$_5$ | 1.7 μM |
| (KR)$_3$ | 23 μM |
| (KR)$_4$GDV | 15 μM |
| (R)$_8$GDV | 3.5 μM |
| (R)$_{11}$ | 7 μM |

Complete inhibition was seen at the following concentrations, shown in Table VI, below.

TABLE VI

| (KR)$_7$ | 12 and 15 μM |
| (KR)$_5$ | 6 and 7 μM |
| (KR)$_3$ | 60 and 120 μM |
| (KR)$_4$GDV | 44 μM |
| (R)$_8$GDV | 24 μM |

EXAMPLE 3

Inhibition of Ristocetin-Induced Platelet Aggregation

The inhibitory activity of the peptides of the present invention was evaluated using washed platelets. The platelets, prepared as described in Trapani-Lombardo et al., *J. Clin. Invest.*, 76, 1950–1958 (1985), were adjusted to a final concentration of $3 \times 10^{11}$. Peptides, at varying concentrations, and purified vWF, at a final concentration of 0.8 μg/ml, were incubated with the platelets for 5 minutes at 37° C. Ristocetin was then added at a final concentration of 1.0 mg/ml. Reaction mixtures were prepared in siliconized glass cuvettes and then placed in a Lumi aggregometer (ChronoLog Corp.) at 37° C. with constant stirring of the platelet suspension at 1200 rpm. Aggregation was quantitated by monitoring the increase in light transmittance through the stirred platelet suspension.

The IC$_{50}$ values (the concentration which inhibited aggregation by 50%, as judged by the percent decrease in the initial slope of the aggregation curve) of the peptides are shown in Table VII, below.

TABLE VII

| | |
|---|---|
| (KR)$_7$ | 3 μM |
| (KR)$_5$ | 50 μM |
| (KR)$_3$ | 250 μM |

At a concentration of 100 μM the following peptides inhibited aggregation to the extent shown in Table VIII, below.

TABLE VIII

| | |
|---|---|
| (KR)$_7$ | 82% inhibition |
| (KR)$_5$ | 50% inhibition |
| (KR)$_3$ | no significant inhibition |
| (R)$_8$GDV | 70% inhibition |

EXAMPLE 4

Inhibition of Asialo-vWF-Induced Aggregation

The inhibitory activity of the peptides of the present invention was determined using platelet-rich plasma prepared by differential centrifugation of blood drawn into 11 mM trisodium citrate anticoagulant. The platelet count was adjusted to $3 \times 10^{11}/1$. The peptides, at a concentration of 55 μM, were incubated with platelet rich plasma for 5 minutes at 37° C. Asialo-vWF was then added at a final concentration of 15 μg/ml. Reaction mixtures were prepared in siliconized glass cuvettes and then placed in a Lumi aggregometer (ChronoLog Corp.) at 37° C. with constant stirring of the platelet suspension at 1200 rpm. Aggregation was quantitated by monitoring increase in light transmittance through the stirred platelet suspension.

Inhibition of aggregation by the peptides is shown in Table IX, below.

TABLE IX

| | |
|---|---|
| (KR)$_7$ | 100% inhibition |
| (KR)$_5$ | 88% inhibition |
| (KR)$_3$ | no significant inhibition |
| (R)$_8$GDV | 92% inhibition |

EXAMPLE 5

Identification of GPIbα Receptor Sites

It has been previously demonstrated that the amino terminal extracytoplasmic region of the GPIbα chain, extending between residues 1 and 293, contains a domain or domains which interact with vWF in the absence of any other component of the GBIb complex, or any other platelet membrane component, Vicente et al.

The studies of the present application were designed to identify the receptor sites of this interaction. The entire amino acid sequence of this 45 kDa binding fragment was reproduced as a series of 27 overlapping synthetic peptides which were used in vWF binding inhibition assays.

Percent inhibition of binding of vWF to platelets was measured using $I^{125}$ labelled vWF prepared according to the methods of Ruggeri et al. See also DeMarco et al., *J. Clin. Invest.*, 68, 321-328 (1981). Binding of vWF to platelets induced by ristocetin and/or botrocetin (and inhibition thereof) was measured according to the method of MacFarlane et al., *Thromb. Diath. Haemorrh.*, 34, 306-308 (1975) which utilizes washed platelets fixed with formaldehyde. FIG. 1a shows the amino acid sequence of the amino terminal region of GPIbα in one-letter notation. T$_1$ indicates the site of tryptic cleavage that gives origin to the 45 kDa domain. Numerals above the sequence line indicate the first residue in a synthetic peptide sequence, and the same number below the sequence line indicates the last residue in that peptide. The heavy bar underlines the sequence of the longer peptide (29 residues) used in subsequent studies. FIG. 1b displays in a bar graph the inhibitory effect of all the peptides tested on ristocetin-dependent (black bars) and botrocetin-dependent (hatched bars) vWF binding to GPIb-IX. Each peptide, used at a final concentration of 500 μmol/l with a $^{125}$I-vWF concentration of 2 μg/ml, is identified by the same numeral used in the top part of the figure. Note that ristocetin-dependent binding was inhibited by five groups of peptides (mainly those identified by numbers 3-4, 7-9, 14, 21, and 23-25), while botrocetin-dependent binding was significantly inhibited only by peptides 7-10 and 19-25. Peptide 25 shows the most promise as an inhibitor based on both assay systems.

EXAMPLE 6

Activity Assay of the GLY$^{271}$ to GLU$^{285}$ Fragment

Reference to FIG. 1, discussed in the previous example, indicates that peptide 25, representing the sequence GLY$^{271}$ to GLU$^{285}$ of glycocalicin, shows excellent promise as an inhibitor of vWF binding.

Figure 2A:
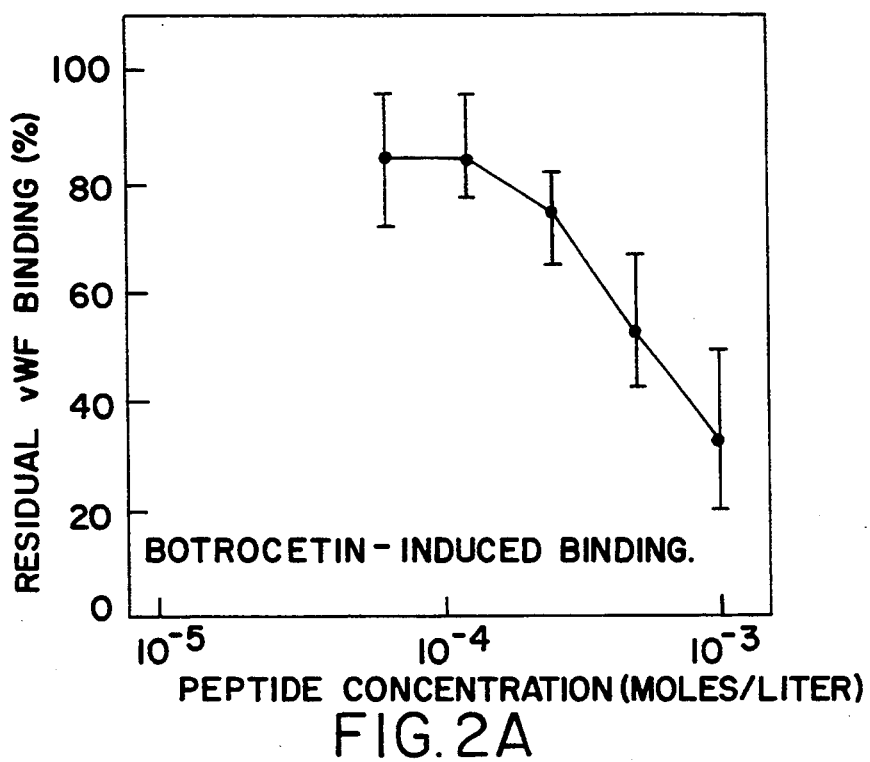
FIGS. 2A and 2B are a pair of graphs which show the inhibitory effect of the GPIbα peptide fragment consisting of residue positions 271 to 285 on (A) botrocetin-dependent and (B) ristocetin-dependent vWF binding to platelet GPIb receptors.
Figure 2B:
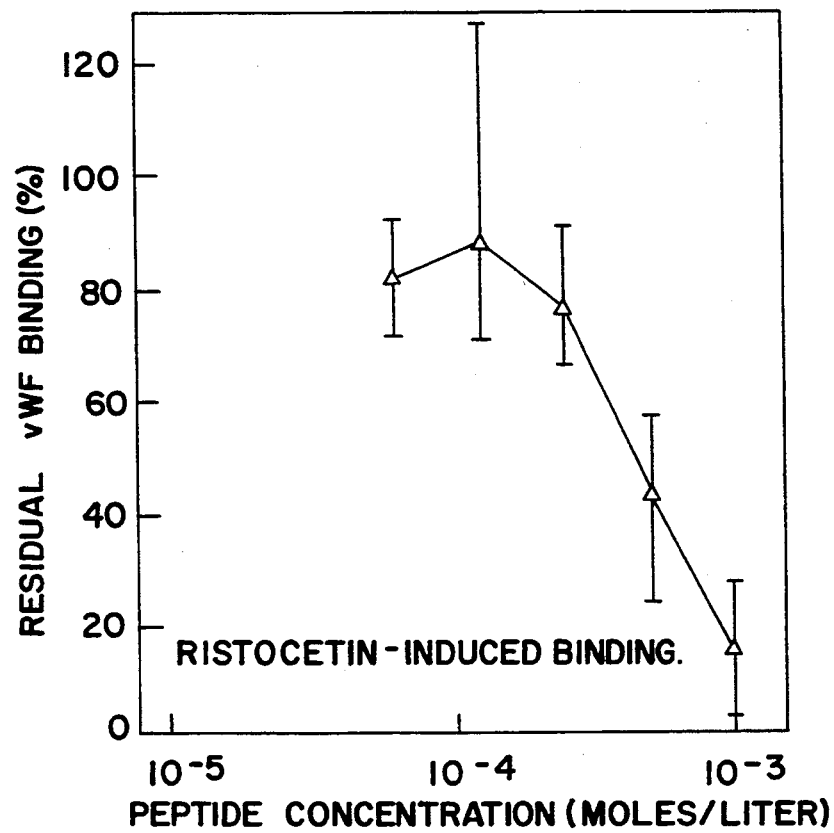

Further experiments were performed with a constant $^{125}$I-vWF concentration of 2 μg/ml and varying peptide concentration, as indicated on the FIG. 2 abscissa. The top panel shows the mean and range of three determinations of residual vWF binding in the presence of botrocetin; the lower panel, mean and range of five determinations in the presence of ristocetin. Residual binding was calculated after subtracting from each experimental point the value measured in the presence of a saturating amount of the anti-GPIb monoclonal antibody LJ-Ibl. One hundred percent binding was that measured in the presence of Hepes buffer instead of peptide.

EXAMPLE 7

Activity Assay of the SER$^{251}$ to TYR$^{279}$ Fragment

Reference to FIG. 1 (corresponding to example 5) demonstrates that peptides 23 through 25 have improved binding relative to synthetic peptide 26. Since the amino acid sequence of peptides 26 and 25 overlap, it was postulated that constructing a peptide which omitted the terminal portion of peptide 26 would yield a peptide showing significant inhibitory activity. Accordingly a synthetic peptide constituting the glycocalicin sequence SER$^{251}$ through TYR$^{279}$ was constructed and tested.

Binding inhibition experiments were conducted analogous to those in Example 6 using an I$^{125}$-vWF concentration of 2 μg/ml. The mean and range of two separate binding inhibition experiments are indicated in FIG. 3.

Comparison of the various peptides mentioned in the above examples shows that the most active of the original 26 synthetic peptides is number 25 which inhibits 50% of ristocetin-induced binding of vWF at a concentration of 420 μM, and 50% of botrocetin-induced binding at 530 μM. In contrast, the peptide of this example, representing residues 251-279, inhibits 50% of ristocetin induced binding at a concentration of 170 μM.

The basis for designing synthetic polypeptide inhibitor molecules which have a high probability to bind vWF (because the selected domains occur on the surface of the native GPIbα chain), and which use inert linker sequences to connect specific glycocalicin domains, is demonstrated by the method of Emini et al., *J. of Virology*, 55, 836–839 (1985). These surface probability index calculations show that 13 of the 15 amino acids in peptide 25, and 12 positions in the peptide of this example, have a surface probability index greater than four.

It is further postulated that since the peptide of this example contains a cysteine capable of dimerization, and dimers are indeed the prevalent form under the temperature, pH, and time conditions of vWF binding assays, as shown by reverse phase HPLC, that such dimerization confers upon the peptide structural alterations which enhance its binding to vWF when compared to non-dimerized peptides.

EXAMPLE 8

Design of Complex Synthetic Polymers

Reference to FIG. 1b and Example 5 demonstrates that peptide 8 and peptide 25 represent effective domains from which to design complex synthetic polymers containing vWF binding regions and inert spacer or linker sequences so that multimeric vWF complexes can be maximally inhibited.

EXAMPLE 9

GPIbα (HIS$^1$-LEU$^{610}$) Expression in Stable Mammalian Transformants

Step 1. Construction of a DNA Sequence for Expression of the Mature His$^1$-Leu$^{610}$ Polypeptide Based on the published GPIbα cDNA sequence of Lopez et al., two flanking oligonucleotides were synthesized for the amplification in a polymerase chain reaction of a region of the GPIbα gene which it was believed would be suitable as a probe to screen a human genomic lambda (λ) phage library.

Accordingly, human genomic DNA was subjected to enzymatic amplification in a polymerase chain reaction according to the method of Saiki et al., *Science*, 239, 487–491 (1988). The procedure utilizes a double stranded GPIbα DNA sequence, a subsegment of which is to be amplified, and two single stranded oligonucleotide primers which flank the ends of the subsegment. The primer oligonucleotides (in the presence of a DNA polymerase and deoxyribonucleotide triphosphates) were added in much higher concentrations than the DNA to be amplified. The vast majority of polynucleotides which accumulate after numerous rounds of denaturation, oligonucleotide annealing, and synthesis represent the desired double stranded cDNA subsegment suitable for further propagation by cloning.

PCR reactions were performed with a DNA thermal cycler (Perkin Elmer Co., Norwalk, CT/Cetus Corporation, Berkeley, Calif.) using Taq polymerase (*Thermus aquaticus*). The reactions were run in 100 μl volumes containing 1.0 μg of human genomic DNA, 1.0 μg of each synthetic oligonucleotide primer, and buffer consisting of 50 mM KCl 10 mM Tris-HCl (pH 8.3), 15 mM MgCl$_2$, 0.1% gelatin (BioRad Co., Richmond, Calif.) and 200 mM of each dNTP. PCR conditions were 35 cycles of 30 seconds at 94° C. 30 seconds at 52° C. and 1 minute at 72° C. Amplified fragments were then purified and isolated by electrophoresis through a 2% agarose gel, Maniatis et al., *Molecular Cloning, A Laboratory Manual*, 164–170, Cold Spring Harbor Lab., Cold Spring Harbor, N.Y. (1982).

Specifically, the following oligonucleotides were synthesized by the phosphoramidite method, Sinha et al., *Tetrahedron Letters*, 9-4, 5843 (1983) using a model 380B automated system, Applied Biosystems, Foster City, Calif.

The oligonucleotides selected were:

Oligonucleotide (1) - SEQ ID NO: 2
5' - GAATCTGACAGCGCTGCCTCCAGACCTGCCG - 3'
↑                                    ↑
644                                  674 and

Oligonucleotide (2) - SEQ ID NO: 3
3' - GCGACGGAGAACCACGGGAC - 5'
↑                        ↑
925                      944

5' - cgctgcctcttggtgccctg - 3'

Oligonucleotide (1) is equivalent to non-transcribed strand DNA (coding strand) for nucleotides 644–674 (using the numbering system for the GPIbα gene of Wenger).

Oligonucleotide (2) is shown 3'→5' and is equivalent to the transcribed strand (noncoding DNA). The corresponding coding strand is shown 5'→3' in lower case letters.

T$_4$ kinase was used to add phosphate groups to each end of the amplified fragment. T$_4$ ligase was used to blunt end ligate the fragment into the SmaI site within the multiple cloning sequence of the double stranded replicative form of M13mp18 bacteriophage. The ability to isolate a stable single stranded (+) form of the virus is particularly useful to verify the integrity of any cloned sequences therein. See Messing, *J. Meth. Enzymology*, 101, 20–78 (1983), and Yanish-Perron et al., *Gene*, 33, 103–109 (1985). Accordingly, the GPIbα DNA insert was completely sequenced using single stranded dideoxy methodology (Sanger et al., *Proc. Natl. Acad. Sci. USA*, 74, 5463–5467 (1977) utilizing the single stranded (+) form of M13mp18. Sequencing in M13mp18 established that the GPIbα insert was 301 base pairs in length, indicating that the corresponding cDNA region, Lopez et al., did not involve an intron boundary. The 301 base pair (bp) fragment was then subjected to nick translation for incorporation of $^{32}$P-labelled nucleotides, thus converting the fragment into a radiolabelled probe, Rigby et al., *J. Mol. Biol.*, 113, 237 (1977).

A human genomic λ phage library (using Lambda Fix ™, Stratagene, La Jolla, Calif.) was prepared using an EcoRI partial digest of human cell DNA. The library was screened following the hybridization and plaque purification procedure of Benton et al., *Science*, 196, 180–182 (1977) using *E. coli* strain LE 392 as host. Screening with the 301 bp fragment resulted in the isolation of 6 positive clones after 4 cycles of plaque purification.

In order to conduct the library screening for each positive clone, an appropriate dilution of λ phage was incubated with bacteria at 37° C. for 20 minutes with constant shaking. Melted agarose was added to this mixture and the entire contents spread onto a petri dish with a hard agar base. The plates were incubated overnight at 37° C. An imprint of the bacteriophage plaques thus obtained was produced by gently placing a nitrocellulose filter onto the surface of the plate. Phage particles and DNA were transferred to the filter by capillary action in an exact replica of the pattern of plaques. After denaturation with NaOH, the DNA was irreversibly bound to the filter by baking and was then hybridized to the $^{32}$P-labelled probe. Unbound probe was washed away and the filters were exposed to film. Plaques which were positive for hybridization were identified by aligning the film with the original agar plate. These plaques were individually picked and amplified. In general the initial plating density of phage was such that individual plaques could not be picked but instead an area comprising several different phage species was picked. This mixture was amplified and replated at low density to be rescreened to determine which initial positives were true positives and to "plaque" purify each positive. After 3 rounds of such rescreening individual positively hybridizing phage were isolated for further characterization.

Purified λ DNA was then isolated from each positive λ clone by precipitating phage from respective lysed *E. coli* LE 392 samples following the procedure of Maniatis et al., at 76–85.

One μg samples of DNA from each of the six positive λ clones were then digested with EcoRI. The EcoRI digests were then separated according to molecular weight by electrophoresis in agarose, followed by transfer to nitrocellulose for detection by autoradiography using the $^{32}$P-labelled 301 bp fragment. Southern, *J. Mol. Biol.*, 98, 503 (1975). An approximate 6000 base pair EcoRI fragment was recognized.

The approximate 6000 base pair fragment visualized and extracted from an agarose gel was then cloned into pBluescript KS- plasmid (Stratagene Co., La Jolla, Calif.) at its EcoRI site. The plasmid was then propagated in *E. coli* strain XL-1 Blue (Stratagene Co.). Plasmids were recovered from host *E. coli* by an alkaline cell lysis procedure, Birnboim and Doly, *Nucleic Acids Research*, 7, 1513 (1979) followed by purification by CsCl/ethidium bromide equilibrium centrifugation according to Maniatis et al., at 1.42.

Plasmid so isolated was then digested with BamHI and BglII creating a 2161 base pair fragment (nucleotides 503 to 2663 using the numbering system of Wenger et al.) which fragment extends from upstream above the initiating MET$^1$ codon (nucleotides 537–539) to downstream below the LEU$^{610}$ codon (nucleotides 2412–2414) and the TGA translation stop codon (2415–2417). The BamHI site of the fragment corresponds to nucleotides 502–507 and the BglII site thereof nucleotides 2658–2664.

The 2161 bp fragment was then cloned into the BamHI site of pBluescript KS- (Strategene Co., La Jolla, Calif.) as a BamHI-BglII fragment. Since BamHI and BglII restriction sites contain identical internal sequences GATC/CTAG, a BglII restricted site may be annealed into a BamHI site. The fragments were ligated with T$_4$ DNA ligase, however the integrity of the affected BglII end was not restored. Hybridization with the 301 base pair probe and sizing on agarose were repeated. The plasmids were propagated in *E. coli* XL-1 Blue.

Restriction mapping was then performed to select a clone of *E. coli* XL-1 Blue (Stratagene) in which the GPIbα DNA within a contained pBluescript KS- plasmid possessed an insert orientation such that the XhoI site of the polylinker would be upstream (5') from the insert and the NotI site would be downstream (3') therefrom. The XhoI-NotI fragment was used as follows to create a suitable expression plasmid.

Step 2. Construction of Plasmids for Integration into Mammalian Cells

A selection procedure based on aminoglycosidic antibiotic resistance was designed to select, continuously, for transformants which would retain a suitable GPIbα expression plasmid.

pCDM8 vector, (developed by Seed et al., *Nature*, 329, 840–842 (1987) and available from Invitrogen, San Diego, Calif.) was modified by Dr. Timothy O'Toole, Scripps Clinic and Research Foundation, La Jolla, Calif. to include a neomycin resistance gene (phosphotransferase II) that was cloned into the BamHI restriction site of pCDM8 as a part of a 2000 base pair BamHI fragment.

The protein produced by the neomycin (neo) gene also confers resistance against other aminoglycoside antibiotics such as Geneticin ® G418 sulfate (Gibco/Life Technologies, Inc., Gaithersburg, Md.).

Several other suitable expression vectors containing neomycin resistance markers are commercially available. Examples include pcDNA 1$^{neo}$ (Invitrogen, San Diego, Calif.), Rc/CMV (Invitrogen, San Diego, Calif.) and pMAM$^{neo}$ (Clontech, Palo Alto, Calif.). If necessary the GPIbα fragment may be differently restricted or modified for expression capability in these other expression plasmids.

The XhoI-NotI fragment from pBluescript KS- plasmid was inserted into pCDM8$^{neo}$ which had been restricted with XhoI and NotI. Ampicillin sensitive *E. coli* strain XS-127 cells (Invitrogen, La Jolla, Calif.) were transformed with the resultant ligated DNA mixture following the method of Hanahan, *J. Mol. Biol.*, 166, 557–580 (1983).

Plasmids from resultant colonies were characterized by restriction mapping and DNA sequencing to identify colonies which contained the intended insert. One such plasmid (designated pMW1), was maintained in *E. coli* strain XS-127, and was selected for mammalian cell transformation procedures.

Prior to use in transforming mammalian cells, supercoiled plasmids (pMW1) were recovered from host *E. coli* by the alkaline cell lysis procedure of Birnboim and Doly followed by purification by CsCl/ethidium bromide equilibrium centrifugation according to Maniatis et al., at 1.42.

Step 3. Transformation of Chinese Hamster Ovary Cells pMW1 was introduced into CHO-K1 Chinese hamster ovary cells (ATCC-CCL.61) by a standard calcium phosphate-mediated transfection procedure. Chen et al., *Mol. Cell. Biol.*, 7 (8), 2745–2752 (1987).

CHO-K1 cells were grown to confluence at 37° C. in Dulbecco's modified Eagle's medium (DMEM) (Gibco/Life Technologies, Inc., Gaithersburg, Md.) supplemented with 10% heat-inactivated fetal calf serum (FCS, Gibco), 0.5 mM of each nonessential amino acid (from NEAA supplement, Whittaker, Walkersville, Md.) and 2.5 mM L-glutamine under a 5% $CO_2$ atmosphere, trypsinized as elaborated below, and then subcultured 24 hours prior to transformation at a density of $1.25 \times 10^5$ cells per 60 mm tissue culture dish (approximately 25% of confluence). CHO-K1 cells have a doubling time in DMEM/10% FCS of approximately 16 hours under these conditions.

To accomplish transformation, pMW1 plasmids were recovered from cultures of *E. coli* strain XS-127, according to the method of Birnboim and Doly. 10 μg of plasmids was applied to the cells of each 60 mm dish in a calcium phosphate solution according to the method of Chen et al. After inoculation with plasmid the cells were maintained in DMEM/10% FCS at 37° C. in a 5% $CO_2$ atmosphere.

Approximately 48 hours post-transfection and after growth at 37° C. in a 5% $CO_2$ atmosphere, the cells were trypsinized as follows. Growth medium for each dish was replaced by 3 ml of a solution of phosphate-buffered saline (37 mM NaCl, 27 mM KCl, 4.3 mM $Na_2HPO_4.7H_2O$/1.4 mM $K_2HPO_4$, pH 7.4) containing also 0.25% trypsin, 0.2% (w/v) EDTA. Trypsinization was conducted for 3 minutes. The trypsin-containing medium was removed and the dishes were then placed in the incubator for a further 15 minutes after which the cells were resuspended in DMEM containing 10% FCS The cells from each dish were then split 20 fold, and plated at a density of approximately $1.2 \times 10^4$ cells/60 mm dish (approximately 2% of confluence).

Production of stable transformants, which have integrated the plasmid DNA, was then accomplished by adding Geneticin ® G418 sulfate to the 60 mm dishes to a concentration of 0.8 mg/ml. Growth was continued for 14 days at 37° C. in a 5% $CO_2$ atmosphere. Surviving independent colonies were transferred to 12 well plates using cloning rings and then grown for another seven days in DMEM/10% FCS supplemented with 0.8 mg/ml of Geneticin ®. Under these conditions 3 to 7 surviving colonies per plate were apparent after 10-14 days. Approximately 100 stable transformants can be isolated from each original 60 mM dish originally containing approximately $5 \times 10^5$ cells at a plate density of approximately 70% of confluence.

Based on screening with the LJ-P3 anti GPIbα monoclonal antibody, more than 50 percent of G418-resistant cell lines produce mature GPIbα polypeptide. The specific geometry of integration of each clone presumably prevents expression in all cases. Stable transformants were then cultured and maintained at all times in medium containing Geneticin ® G418 sulfate (0.8 mg/ml) to apply continuous selection.

Colonies expressing the recombinant mature GPIbα polypeptide were detected by dot-blot analysis on nitrocellulose after lysis in buffer. As a control, recombinant cell extracts were compared with that from nontransfected CHO-K1 cells.

To prepare cell extracts, non-transfected or transfected CHO-K1 cells were harvested with 3.5 mM EDTA and resuspended in 0.25M Tris-HCl pH 7.5 ($10^3$ cells/μl). Cells were lysed by three cycles of freezing and thawing and centrifuged at 12,000 g to remove cell debris. The resulting supernatant was kept at $-70°$ C. as cell extract.

To prepare samples of culture medium containing secreted GPIbα antigen, 80% confluent non-transformed or transformed CHO cells grown in medium containing FCS were washed once with serum-free medium, and then fed with serum-free medium supplemented with L-glutamine and nonessential amino acids. After 24 hours, the medium was collected and centrifuged at 12,000 g to remove cell debris. The corresponding supernatants were pooled and stored at $-70°$ C. until used.

Monoclonal antibodies LJ-Ib1 and LJ-P19, Handa et al., which recognize GPIbα native conformation were used as primary antibody. The secondary antibody ($^{125}$I-rabbit anti-mouse IgG) which had been labelled by the method of Fraker et al., *Biochem. Biophys. Res. Commun.*, 80, 849–857 (1978) was incubated for 2 hours at 25° C. on a nitrocellulose sheet. After rinsing, the nitrocellulose was developed by autoradiography to identify colonies expressing the GPIbα polypeptide.

EXAMPLE 10

Expression of a $HIS^1$-$ALA^{302}$ GPIbα Fragment in Stable Mammalian Transformants This example demonstrates conditions under which a DNA sequence encoding the fragment of mature GPIbα polypeptide having an amino terminus at $HIS^1$ and a carboxy terminus at residue $ALA^{302}$ thereof may be expressed in and secreted from cultured mammalian cells.

The following section concerns primer directed amplification of DNA. pBluescript KS- containing at its BamHI site the 2161 base pair fragment (nucleotides 503–2664 according to Wenger et al.) was subjected to enzymatic amplification in a polymerase chain reaction according to the method of Saiki et al., and following generally the procedures of Example 9, above.

The following oligonucleotides were synthesized by the phosphoramidite method, Sinha et al., using a model 380B automated system, Applied Biosystems, Foster City, Calif.

Oligonucleotide (3) - see SEQ ID NO: 4
5' <u>GGATCC</u>ACTCAAGGCTCCCTTGCC 3'
BamHI (nucleotide positions 502–525)

Oligonucleotide (4) - see SEQ ID NO: 5

3' CAG TTC AAG GGG TGG TTT CG 5'  ⟵ link with BamHI

5' gtc aag ttc ccc acc aaa gc 3'
   VAL LYS PHE PRO THR LYS ALA
   296 297 298 299 300 301 302

(nucleotide positions 1470–1489)

Oligonucleotide (3) is equivalent to nontranscribed (coding) strand DNA. Oligonucleotide (4), shown in capital letters, is equivalent to transcribed (noncoding) strand DNA. The corresponding coding strand for oligonucleotide (4) is shown 5'→3' with the encoded amino acids shown by standard three letter designation.

A BamHI linker was added to the amplified double stranded DNA sequence 3' to the partial $ALA^{302}$ codon thereby completing the codon and enabling the DNA to function as a BamHI insert. Roberts et al., *Nature*, 265, 82–84 (1977).

The amplified fragment was then cloned into the BamHI site within the multiple cloning sequence of the double stranded replicative form of M13mp19 bacteriophage. The ability to isolate a stable single stranded (+) form of the virus is particularly useful to verify the integrity of any cloned sequences therein. See, for example, Messing and Yanish-Perron et al.

Accordingly, the GPIbα DNA insert was completely sequenced using single stranded dideoxy methodology, Sanger et al., utilizing the single stranded (+) form of M13mp19 to confirm that the GPIbα fragment contained the correct coding sequence for the region of GPIbα DNA represented by nucleotides 502 to 1489 and including a codon for the initiating methionine, the remaining 15 residues of the signal peptide and residues 1 to 302 of the amino terminal region of mature GPIbα polypeptide.

Sequencing in M13mp19 established numerous clones having insert orientation at the BamHI site suitable for expression from pCDM8$^{neo}$ plasmid. The GPIbα sequence of one such clone was removed from M13mp19 as an EcoRI (5') - XbaI (3') fragment which was then cloned into the polylinker region of pBluescript KS-. An XhoI (5') - NotI (3') fragment of this second insert was then removed from pBluescript KS- and cloned into pCDM8$^{neo}$, which had been restricted with Xho and NotI, following the procedures used for insertion of pMW1 (see Example 9).

Ampicillin sensitive *E. coli* strain SX-127 cells (Invitrogen, San Diego, Calif.) were transformed with the resultant ligated DNA mixture following the method of Hanahan.

Plasmids from resultant colonies were characterized by restriction mapping and DNA sequencing to identify colonies which contained the intended insert. One such appropriate plasmid (designated pMW2) was maintained in *E. coli* strain XS-127, and was selected for mammalian cell transformation procedures.

Prior to use in transforming mammalian cells, supercoiled plasmids (pMW2) were recovered from host *E. coli* by the alkaline lysis procedure of Birnboim and Doly followed by CsCl/ethidium bromide equilibrium centrifugation according to the procedure of Example 9. Transformation of CHO-K1 cells also followed the procedure of Example 9 for pMW1 plasmid.

EXAMPLE 11

Demonstration of Native Tertiary Structure in the Polypeptide Produced by pMW1 and pMW2 Plasmids The presence of GPIbα antigen in stable transformant cells (containing pMW1 or pMW2 plasmid) was demonstrated by applying cell lysates or culture medium from CHO-K1 containing dishes (both prepared as in Example 9) to nitrocellulose.

10 μl aliquots of lysate or culture medium were spotted onto nitrocellulose membranes (0.45 micron pore size, Bio-Rad, Richmond, Calif.) and air dried. The membrane was then soaked with constant shaking for 2 hours at 22°–25° C. in "Blotto" (5 mg/ml fat-free dry milk, 0.25 mM phenylmethyl sulfonyl fluoride, 0.15M NaCl in phosphate buffer pH 7.3), a protein blocking solution to inhibit nonspecific interaction.

The membrane was then incubated with native GPIbα conformation-requiring monoclonal antibody (5–10 μg/ml of LJ-Ib1 or LJ-P19) for two hours at 22°–25° C. After washing 3 times with Blotto, the membrane was transferred to a solution of $^{125}$I-labelled rabbit anti-mouse IgG (0.08–0.16 mCi I$^{125}$ per dot) and incubated for 2 hours at 22°–25° C. The wash with Blotto was repeated 3 times prior to drying and making the autoradiograph (using Kodak AR film).

Figure 4:
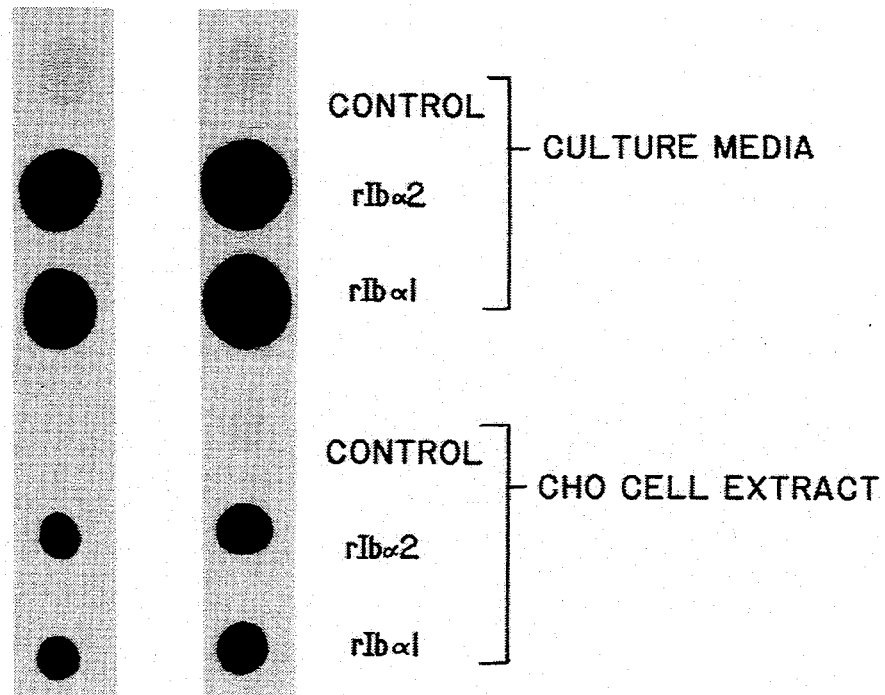
FIG. 4 is a dot blot profile demonstrating the reactivity of GPIbα polypeptides, produced by pMW1 and pMW2 transformed cells, to conformation dependent anti-GPIbα monoclonal antibodies.

FIG. 4 demonstrates results with LJ-Ib1 and LJ-P19 primary antibody using cell extract or culture medium from pMW1 and pMW2 transformed cells. Cell extract and culture medium from untransformed CHO cells were used as controls. FIG. 4 demonstrates that ribα1 antigen and ribα2 antigen (produced by pMW1 and pMW2 transformants respectively), whether isolated from cell lysates or culture medium, present domains of tertiary conformation present in native GPIbα. Similar results were obtained using another conformation dependent anti-GPIbα monoclonal antibody, LJ-P3.

EXAMPLE 12

Intracellular Processing of the GPIbα Polypeptide Produced by pMW2 Plasmid

Polypeptides produced by pMW2-transformed CHO-K1 cells from a representative cell line were characterized under reducing conditions by immunoblotting ("Western blotting") following the procedure of Handa et al. See also Burnett et al., *A. Anal. Biochem.*, 112, 195–203 (1981).

The disulfide bonds of the pMW2 polypeptides were reduced prior to electrophoresis by treatment with 30 mM dithiothreitol at 37° C. for 1 hour in the absence of denaturing agents. Electrophoresis was performed on a sodium dodecylsulfate polyacrylamide 10% gel (SDS-PAGE) and protein samples were then stained with Coomassie Brilliant Blue. Protein bands from duplicate gels were transferred to nitrocellulose (0.45 micron pore size, BioRad, Richmond, Calif.) using 350 milliamperes per gel at 3° C. for 18 hours. GPIbα antigenic material was visualized by first incubating the nitrocellulose membrane with LJ-Ib1 monoclonal antibody, the epitope of which has been previously identified on the reduced 35 kDa amino terminal fragment of GPIbα, Vicente et al.

Immunoreactive bands were visualized using $^{125}$I-rabbit antimouse IgG as secondary antibody, labelled by the method of Fraker et al.

Figure 5:
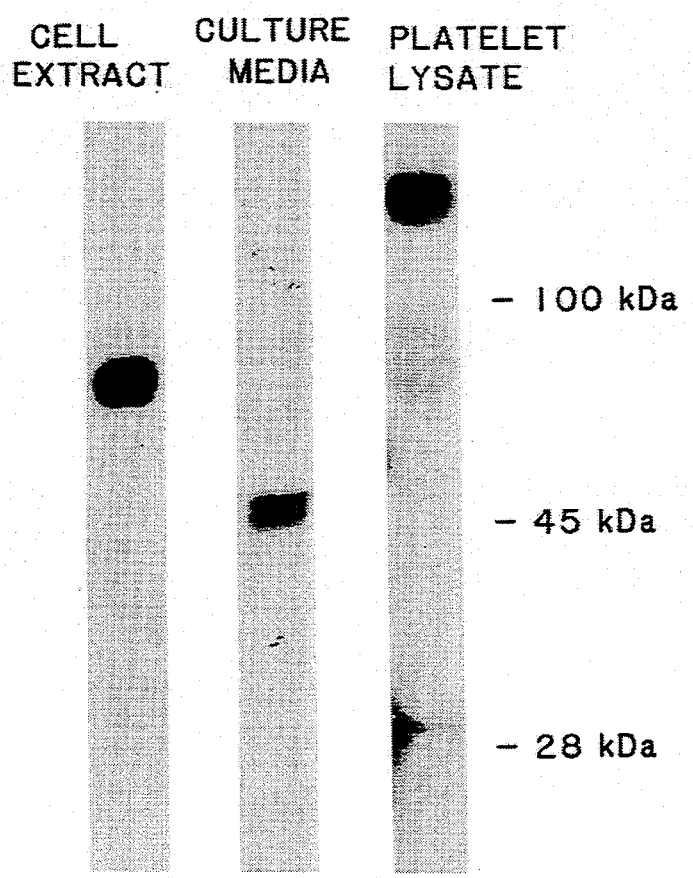
FIG. 5 is an immunoblot showing intracellular processing of the pMW2 polypeptide in host cells.

Extracts from CHO-K1 cells transformed with pMW2 plasmid which were run under reducing conditions reveal a prominent precursor polypeptide species of approximately 60 kDa apparent molecular weight (FIG. 5). Polypeptide from culture medium tested under similar conditions are revealed as a band of approximate 45 kDa apparent molecular weight. Extracts from platelets reveal the expected full length 145 kDa GPIbα polypeptide.

EXAMPLE 13

Botrocetin Induced Binding of $^{125}$I-vWF to the GPIb(α) Polypeptide Produced by pMW2 Plasmid This example demonstrates that the HIS$^1$-ALA$^{302}$ polypeptide produced by CHO-K1 cells stably transformed with pMW2 plasmid is functionally active.

Fifty μl volumes of culture media (DMEM without FCS) from pMW2 transformed CHO-K1 cells (at or near confluence) were placed in microtiter wells with circular nitrocellulose membranes (8 mm diameter) and incubated at room temperature for 30 minutes. The filters were then washed two times with a solution of 20 mM Hepes, pH 7.4, 150 mM NaCl, and 6% bovine serum albumin (HEPES/BSA). To minimize background caused by nonspecific interaction, blocking with HEPES/BSA was continued for 2 days at 4° C.

To initiate the assay, 30 μl volumes of monoclonal anti-GPIbα antibody (resulting in specified final concentrations thereof, FIG. 6) were incubated with the culture mediacoated nitrocellulose membranes for 15 minutes at room temperature. A mixture comprised of 10 μl of $^{125}$I-vWF and 10 μl of botrocetin was preincubated for 5 minutes at room temperature and then added to the microtiter wells for a further 15 minute incubation. The resultant botrocetin concentration was 5 μg/ml.

The filters were then washed 4 times with HEPES/BSA. Bound $^{125}$I radioactivity was then determined for each nitrocellulose filter to measure botrocetin-induced vWF binding to rIbα2.

FIG. 6 demonstrates the functional activity of the HIS$^1$-ALA$^{302}$ GPIbα polypeptide. Anti-GPIbα monoclonal antibody LJ-Ib1 (100 μg/ml) and LJ-Ib10 (100 μg/ml) substantially inhibit rIbα2 polypeptide-vWF interaction as predicted by the fact that LJ-Ib1 and LJ-Ib10 are known inhibitors of GPIbα-vWF interaction. LJ-Ib1 recognizes a native conformation-dependent epitope of GPIbα. Handa, et al., and also Vicente, et al.

FIG. 6 demonstrates also that monoclonal antibodies "LJ-P3" and "229" do not inhibit rIbα2-vWF interaction. This is expected since although antibodies LJ-P3 and 229 have epitopes on GPIbα and vWF respectively, they do not inhibit the binding of vWF to platelets.

We claim:

1. A pCDM8$^{neo}$-based expression vector including the nucleotide sequence encoding the amino acid sequence of the 45 kDa tryptic fragment of glycocalicin, wherein said vector is effective in expressing said fragment in the absence of the expression of glycoprotein Ib$\beta$ in a mammalian host cell.

2. A host cell transformed by a vector according to claim 1.

3. A recombinant DNA expression vector encoding a peptide which inhibits binding of von Willebrand factor to platelet membrane glycoprotein Ib, said vector including a nucleotide sequence encoding the amino acid sequence from HIS$^1$ to LEU$^{610}$, inclusive, of the amino terminal region of platelet membrane glycoprotein Ib$\alpha$, or any sequential subset thereof which inhibits binding of von Willebrand factor to platelet membrane glycoprotein Ib, wherein said vector is effective in expressing said peptide in the absence of the expression of glycoprotein Ib$\beta$ in a mammalian host cell.

4. A vector according to claim 3 wherein said nucleotide sequence encodes said HIS$^1$ amino acid.

5. A vector according to claim 4 wherein said nucleotide sequence encodes amino acid THR$^{294}$ of said platelet membrane glycoprotein Ib$\alpha$.

6. A vector according to claim 5 wherein said nucleotide sequence encodes an amino acid sequence consisting essentially of HIS$^1$ to ALA$^{302}$.

7. A vector according to claim 5 wherein said nucleotide sequence encodes an amino acid sequence comprising HIS$^1$ to LEU$^{610}$.

8. A vector according to claim 5 wherein said nucleotide sequence further encodes a signal polypeptide.

9. A vector according to claim 5 which is derived from pCDM8$^{neo}$.

10. A mammalian host cell transformed by a vector according to one of claims 5, 6 and 7.

11. A host cell according to claim 10 which is capable of expressing and secreting a peptide which includes the amino acid sequence of the 45 kDa tryptic fragment of glycocalicin.

12. A process for producing a peptide which inhibits binding of von Willebrand factor to platelet membrane glycoprotein Ib which includes the amino acid sequence of the 45 kDa tryptic fragment of glycocalicin comprising:

providing a stable, extrachromosomally replicable vector capable of directing in mammalian cells the expression, in the absence of the expression of GPIb$\beta$, of a nucleotide sequence encoding an amino acid sequence which includes said fragment, said nucleotide sequence further encoding as part of said amino acid sequence an amino acid sequence which corresponds to the amino acid sequence of the remaining portion of glycoprotein Ib$\alpha$ or subset thereof, and which is oriented at the carboxy terminus of said fragment; transforming said mammalian cells with said vector; and maintaining said transformed mammalian cells under conditions permitting the expression of said peptide.

13. A process according to claim 12 wherein said vector is pMW2.

14. A process according to claim 12 further comprising the step of recovering said peptide which consists essentially of the 45 kDa tryptic fragment of glycocalicin.

15. A process according to claim 12 wherein said vector is pMW1.

16. An expression vector according to claim 1 wherein said vector is pMW1.

17. An expression vector according to claim 1 wherein said vector is pMW2.

18. A host cell according to claim 2 wherein said cell is a eucaryotic cell.

19. A host cell according to claim 18 wherein said eucaryotic cell is a mammalian cell.

* * * * *